(12) United States Patent
Sparling et al.

(10) Patent No.: US 6,265,567 B1
(45) Date of Patent: Jul. 24, 2001

(54) ISOLATED FRPB NUCLEIC ACID MOLECULE

(75) Inventors: P. Frederick Sparling, Moncure, NC (US); Margaret Beucher, Connelleville, PA (US)

(73) Assignee: University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 08/628,434

(22) Filed: Apr. 5, 1996

Related U.S. Application Data

(63) Continuation-in-part of application No. 08/418,964, filed on Apr. 7, 1995, now abandoned.

(51) Int. Cl.$^7$ .................................................. C12N 15/31
(52) U.S. Cl. ........................................ 536/23.7; 435/69.1
(58) Field of Search ........................... 435/69.1, 320.1; 530/350; 536/23.7

(56) References Cited

PUBLICATIONS

Ley et al. "Sequence variability of FrpB, a major iron–regulated outer–membrane protein in the pathogenic neisseriae", Microbiology. vol. 142, pp 3269–3274, 1996.*
Pettersson et al. "Molecular characterization of the FrpB, the 70–Kilodalton iron–regulated outer membrane protein of *neisseria meningitidis*", Infection and Immunity. vol. 63, No. 10, pp 4181–4184, Oct. 1995.*
Dempsey et al Journal of BActeriology vol. 173 No. 17 5476–5486, Sep. 1991.*
Beucher, M. Dissertation Abstracts International vol. 56, No. 2 p. 624–B, Aug. 1995.*
Sambrook et al Molecular Cloning A Laboratory Manual, Second Edition Cold Spring Harbor Press, pp. 8.46,8.50, 8.51, 1989.*
Dyer et al, Infection and Immunity vol. 56, No. 4, 977–983, Apr. 1988.*
Beucher et al Journal of Bacteriology vol. 177 No. 8 2041–2149, Apr. 1995.*
Ala'Aldeen et al Vaccine vol. 12 No. 6 535–541, 1994.*
Biotechnology Newswatch p. 12 Vaccines for Sexually Transmitted diseases advancing but slowly, May 1995.*
van der Ley et al Microbiology vol. 142 3269–3274, 1996.*
Pettersson et al Infection and Immunity vol. 63, No. 10 4181–4184, Oct. 1995.*
LAzar et al Molecular and Cellular Biology vol. 8 No. 3 1247–1252, Mar. 1988.*
Burgess et al Journal of Cell biology vol. 111 2129–2138, Nov. 1990.*

* cited by examiner

*Primary Examiner*—Donna C. Wortman
(74) *Attorney, Agent, or Firm*—Thomas C. Gallagher

(57) ABSTRACT

The present invention provides an isolated nucleic acid molecule that encodes an amino acid sequence comprising a FrpB protein. The invention also provides vaccine compositions capable of protecting a mammal against infection by *N. gonorrhoeae* or *N. meningitidis* comprising the FrpB protein encoded by the isolated nucleic acid of the invention and a pharmaceutically acceptable carrier.

2 Claims, No Drawings

ISOLATED FRPB NUCLEIC ACID MOLECULE

This specification is a continuation-in-part of Ser. No. 08/418,964 filed Apr. 7, 1995, now abandoned, which is incorporated herein by reference.

This invention was made in the course of work supported by Public Health Service Grant U01 AI31496 and the Genetics Curriculum training grant 5 T32 GM07092 from the National Institutes of Health. Protein sequencing performed at the UCLA Protein Microsequencing Facility was aided by a BRS Shared Instrumentation Grant (I S10RR05554-01) from the National Institutes of Health. Additionally, this work was supported in part by grant 5 R37-AI26837 from the National Institutes of Health. The United States government has certain rights in this invention.

BACKGROUND OF THE INVENTION

FrpB has been described as a 70 kD major iron-regulated, outer-membrane protein common to *N. gonorrhoeae* and *N. menigitidis* (16, 21). The iron uptake systems of *N. meningitidis* and *N. gonorrhoeae* are similar (3,17).

Previous studies showed that FrpB is surface exposed and immunogenic in vivo (1,16, 41). Polyclonal and some monoclonal anti-FrpB antibodies recognize the denatured protein on Western blots of nearly all gonococcal and meningococcal isolates tested (16 and this invention). Other monoclonal antibodies directed against meningococcal FrpB are bactericidal and strain specific (41). Nevertheless, the size of FrpB appears to be well conserved.

FrpB is useful as a vaccine because of its surface exposure (1,16,41), partial antigenic conservation (8,16), and susceptibility to attack by bactericidal antibodies (41). The cloning and sequencing of the frpB gene of this invention has made possible the production of a vaccine against infection in mammals by *N. gonorrhoeae* or *N. meningitidis*.

SUMMARY OF THE INVENTION

The present invention provides an isolated nucleic acid molecule that encodes an amino acid sequence comprising a FrpB protein.

The invention also provides a method of producing a vaccine composition that protects a mammal from infection by *N. gonorrhoeae* or *N. meningitidis* comprising combining the FrpB protein encoded by the isolated nucleic acid of the invention with a pharmaceutically acceptable carrier.

The invention further provides a vaccine composition capable of protecting a mammal against infection by *N. gonorrhoeae* or *N. meningitidis*, the vaccine composition comprising the FrpB protein encoded by the isolated nucleic acid of the invention and a pharmaceutically acceptable carrier.

In addition, the invention provides antibodies directed to an epitope of the FrpB protein encoded by the isolated nucleic acid sequence of the invention.

The invention also provides a method of detecting an antibody specific for *N. gonorrhoeae* or *N. meningitidis* in a sample comprising contacting the sample with a FrpB protein encoded by the isolated nucleic acid sequence of the invention under conditions to form a complex between the polypeptide and the antibody; and detecting any complex so formed.

Furthermore, the invention provides a method of treating a mammal infected by *N. gonorrhoeae* or *N. meningitidis* comprising administering to the mammal an antibody of the invention, wherein the antibody is directed to an epitope of an *N. gonorrhoeae* or *N. meningitidis* FrpB protein.

DETAILED DESCRIPTION OF THE INVENTION

The subject invention provides an isolated nucleic acid molecule that encodes an amino acid sequence comprising at least a portion of a FrpB protein. In one embodiment of this invention, the isolated nucleic acid molecule is DNA. In other embodiments of this invention, the isolated nucleic acid molecule is cDNA or RNA. In a preferred embodiment of this invention, the isolated nucleic acid molecule comprises a sequence that is the same as or substantially the same as at least a portion of the nucleotide sequence shown in (SEQ ID NO: 1). In a more preferred embodiment, the isolated nucleic acid molecule comprises a sequence that is the same as the nucleotide sequence shown in (SEQ ID NO: 1).

The invention also provides a FrpB protein comprising the amino acid sequence (SEQ ID NO: 2) encoded by the isolated nucleic acid molecules described above. Preferably, the amino acid sequence encodes an antigenic, and more preferably, an immunogenic FrpB. As used herein, antigenic means that the FrpB induces specific antibodies in a mammal, and immunogenic means that the FrpB induces an immune response in a mammal.

As used herein, the term "FrpB" means Fe-regulated protein B and encompasses any polypeptide having an amino acid sequence identical, or substantially identical, to the amino acid sequence of a naturally-occurring FrpB, as well as antigenic fragments thereof. The FrpB nucleic acid and amino acid sequences in the various strains of *N. gonorrhoeae* and *N. meningitidis* are homologous, but exhibit slight differences in their sequences, for example, the nucleic acid and amino acid differences between the homologous strains FA19 and FA1090 shown in (SEQ ID NO: 1 and SEQ ID NO: 3), respectively.

In addition, FrpB encompasses equivalent antigenic polypeptides whose amino acid sequence varies from a naturally-occurring FrpB by one or more amino acid, either internally such as a point mutation, or by addition or deletion at the COOH$^-$ terminus or NH$_2$ terminus or both. An amino acid sequence that is substantially the same as another sequence, but that differs from the other sequence by one or more substitutions, additions and/or deletions, is considered to be an equivalent sequence. Preferably, less than 25%, more preferably less than 10%, and most preferably less than 5% of the number of amino acid residues in a sequence are substituted for, added to, or deleted from the proteins of the invention.

For example, it is known to substitute amino acids in a sequence with equivalent amino acids. Groups of amino acids generally considered to be equivalent are:

(a) Ala(A) Ser(S) Thr(T) Pro(P) Gly(G);
(b) Asn(N) Asp(D) Glu(E) Gln(Q);
(c) His(H) Arg(R) Lys(K);
(d) Met(M) Leu(L) Ile(I) Val(V); and
(e) Phe(F) Tyr(Y) Trp(W).

Such FrpB equivalents include analogs that induce an immune response in a mammal comparable to that of natural FrpB. In addition, such equivalents are immunologically cross-reactive with their corresponding FrpB protein.

A FrpB protein fragment preferably contains sufficient amino acid residues to define an epitope of the antigen. The fragment may, for example, be a minigene encoding only the epitope. Methods for isolating and identifying immunogenic fragments from known immunogenic proteins are described by Salfeld et al. (72) and by Isola et al. (73).

If the fragment defines a suitable epitope, but is too short to be immunogenic, it may be conjugated to a carrier molecule. Some suitable carrier molecules include keyhole limpet hemocyanin, Ig sequences, TrpE, and human or bovine serum albumen. Conjugation may be carried out by methods known in the art. One such method is to combine a cysteine residue of the fragment with a cysteine residue on the carrier molecule.

In a preferred embodiment, FrpB of FA19 is or is an equivalent of the approximately 73 kD outer membrane FrpB protein that is part of the iron regulon of *Neisseria gonorrhoeae* or of *Neisseria meningitidis*. Determinations whether two amino acid sequences are substantially homologous may be based on FASTA searches in accordance with Pearson and Lipman (74).

The FrpB of the present invention may be prepared by methods known in the art. Such methods include, for example, (a) isolating FrpB directly from *Neisseria gonorrhoeae* or *Neisseria meningitidis*; and (b) using the nucleic acid molecule of the invention encoding FrpB to produce recombinant FrpB.

(a) Direct Isolation of FrpB

The FrpB may be isolated directly from *Neisseria gonorrhoeae* or *Neisseria meningitidis* by methods known in the art. First, gonococcal or meningococcal outer membranes are isolated and prepared by known methods. The methods described by West and Sparling (75) and by Schryvers and Morris (76) are suitable.

The isolated membrane FrpB proteins or fragments may be solubilized by known methods, such as the addition of detergents. Commonly used detergents include Octyl-B-Glucoside, Chaps, Zwittergent 3.14 or Triton-X. The use of detergents to enhance solubility of membrane proteins is described by Jones et al. (77), Helenius et al. (78), and Hjelmeland and Chrambach (79).

The FrpB proteins or fragments are isolated from the solubilized membrane fraction by standard methods. Some suitable methods include precipitation and liquid chromatographic protocols such as ion exchange, hydrophobic interaction and gel filtration. See, for example, Methods Enzymol. (80) and Scopes (81).

Purified material may also be obtained by separating the protein or fragment on preparative SDS-PAGE gels, slicing out the band of interest and electroeluting the protein from the polyacrylamide matrix by methods known in the art. The detergent SDS is removed from the protein by known methods, such as by dialysis or the use of a suitable column, such as the EXTRACTI-GEL column from Pierce.

(b) Using Nucleic Acid Molecule of the Invention to Produce FrpB

Alternatively, recombinant methods known in the art may be used for preparing FrpB. For example, FrpB may be produced from the isolated or synthesized nucleic acid molecule of the invention that encodes at least a portion of FrpB; cloning the DNA in a suitable host; expressing the DNA in the host; and harvesting FrpB. (See Sambrook et al. (82)).

Using standard methods of nucleic acid isolation, DNA can be obtained from strains that have been deposited with the American Type Culture Collection, 10801 University Boulevard, Manassas, Va. 20110-2209. FA1090 (ATCC Accession No. 55756) was deposited on Apr. 8, 1996, in accordance with the Budapest Treaty. Strain FA19 (ATCC Accession No. 55073) was deposited earlier on Jul. 12, 1996, also in accordance with the Budapest Treaty.

The DNA may also be synthesized chemically from the four nucleotides in whole or in part by methods known in the art. Such methods include those described by Caruthers in Science 230, 281–285 (1985).

If necessary a full length DNA may also be produced by preparing overlapping double-stranded oligonucleotides, filling in the gaps, and ligating the ends together. The DNA may be cloned in a suitable host cell and expressed. The DNA and protein may be recovered from the host cell. See, generally, Sambrook et al, "Molecular Cloning," Second Edition, Cold Spring Harbor Laboratory Press (1987).

The invention provides a vector which comprises the nucleic acid molecule described above which encodes an amino acid sequence comprising at least a portion of FrpB. Suitable vectors comprise, but are not limited to, a plasmid or a virus. This vector may be transfected into a suitable host cell to form a host vector system for the production of FrpB or of a polypeptide having the biological activity of at least a portion of a FrpB antigenic polypeptide.

Cloning vectors may comprise segments of chromosomal, non-chromosomal and synthetic DNA sequences. Some suitable prokaryotic vectors include plasmids from *E. coli*, such as colE1, pCR1, pBR322, pMB9, and RP4. Prokaryotic vectors also include derivatives of phage DNA such as M13, f1, and other filamentous single-stranded DNA phages.

Vectors for expressing proteins in bacteria, especially *E. coli*, are also known. Such vectors include pK233 (or any of the tac family of plasmids), T7, and lambda $P_L$. Examples of vectors that express fusion proteins include the PATH vectors described by Dieckmann and Tzagoloff (83). These vectors contain DNA sequences that encode anthranilate synthetase (TrpE) followed by a polylinker at the carboxy terminus. Other expression vector systems are based on beta-galactosidase (pEX); maltose binding protein (pMAL); and glutathione S-transferase (pGST)—see Gene (84) and Peptide Research (85).

Vectors useful in yeast are available. A suitable example is the $2\mu$ plasmid.

Suitable vectors for use in mammalian cells are also known. Such vectors include well-known derivatives of SV-40, adenovirus, retrovirus-derived DNA sequences and vectors derived from combination of plasmids and phage DNA.

Further eukaryotic expression vectors are known in the art (e.g., P. J. Southern and P. Berg (86); S. Subramani et al (87); R. J. Kaufmann and P. A. Sharp (88); S. I. Scahill et al (89); G. Urlaub and L. A. Chasin (90).

The expression vectors preferably contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of f1 coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

Suitable expression hosts include well-known prokaryotic and eukaryotic cells. Some suitable prokaryotic hosts include, for example, *E. coli*, such as *E. coli* SG-936, *E. coli* HB 101, *E. coli* W3110, *E. coli* X1776, *E. coli* X2282, *E. coli* DHI, and *E. coli* MRCI, Pseudomonas, Bacillus, such as *Bacillus subtilis*, and Streptomyces. Suitable eukaryotic cells include yeasts and other fungi, insect, animal cells, such as COS cells and CHO cells, human cells and plant cells in tissue culture.

Vaccines

FrpB encoded by a nucleic acid molecule of this invention has particular utility as a vaccine that protects a mammal from infection by *N. gonorrhoeae* or *N. meningitidis*, since the FrpB unexpectedly induces an effective immune response when presented to the immune system that protects from or prevents infection by *N. gonorrhoeae* or *N. meningitidis*. To protect from infection by *N. gonorrhoeae*, the FrpB is preferably substantially the same, as defined above, as at least a portion of the FrpB of *N. gonorrhoeae*. To protect from infection by *N. meningitidis*, the FrpB is preferably substantially the same, as defined above, as at least a portion of the FrpB of *N. meningitidis*. The immune response may also produce a therapeutic effect in an already infected mammal. The mammal is preferably a human.

The invention provides a vaccine composition which comprises the FrpB protein encoded by a nucleic acid of the invention and a pharmaceutically acceptable carrier, such as saline, sterile water, phosphate buffered saline solution, liposomes and emulsions. Other buffering and dispersing agents and inert non-toxic substances suitable for delivery to a mammal may be incorporated in the vaccine composition and are well known to those skilled in the art. The compositions may be sterilized by conventional sterilization techniques.

Adjuvants, which facilitate stimulation of the host's immune response, may be used in the vaccine compositions. Such adjuvants may include, for example, muramyl peptides, lymphokines, such as interferon, interleukin-1 and interleukin-6, or bacterial adjuvants. The adjuvant may comprise suitable particles onto which the mutant or wild-type FrpB protein is adsorbed, such as aluminum oxide particles. These vaccine compositions containing adjuvants may be prepared as is known in the art.

The concentration of FrpB in the composition may vary depending on, for example, fluid volume or antigenicity, and in accordance with the particular mode of administraton chosen.

The invention further provides a method of protecting a mammal against infection by *N. gonorrhoeae* or *N. meningitidis* comprising administering to the mammal the vaccine composition of the invention. The vaccine may be administered to a mammal by methods known in the art. Such methods include, for example, oral, intravenous, intraperitoneal, subcutaneous, intramuscular, topical, or intradermal administration.

This invention also provides a method of producing the above vaccine composition by combining FrpB with a pharmaceutically acceptable carrier, and preferably, also with an adjuvant, as defined above.

FrpB Antibodies

The invention provides antibodies raised against FrpB epitopes encoded by at least a portion of the isolated nucleic acid sequence of the invention. The antibodies are preferably monoclonal. Monoclonal antibodies may be produced by methods known in the art. These methods include the immunological method described by Kohler and Milstein (91) and the recombinant DNA method described by Huse et al. (92).

Mammals infected with *N. gonorrhoeae* or *N. meningitidis* may be treated by administering an antibody of the invention. Preferably, an antibody raised against a polypeptide comprising an amino acid sequence present in *N. gonorrhoeae* or *N. meningitidis* is preferred.

For therapeutic purposes, the antibodies are preferably neutralizing antibodies that significantly inhibit the growth of or kill the bacterial cells in vitro or in vivo. Growth of the bacteria is significantly inhibited in vivo if the inhibition or neutralization is sufficient to prevent or reduce the symptoms of the disease of a mammal infected with the disease.

Neutralizing antibodies may also be used to produce anti-idiotypic antibodies useful as vaccines for immunizing mammals infected with *N. gonorrhoeae* or *N. meningitidis*. Anti-idiotypic antibodies are prepared in accordance with methods known in the art.

Detecting FrpB Using Probes

The invention also provides a method of detecting FrpB in a sample using a probe specific for a FrpB polypeptide. The probe may be an antibody described above. Methods are known for detecting polypeptides with antibodies. For example, a polypeptide may be immobilized on a solid support. Immobilization of the polypeptide may occur through an immobilized first antibody specific for the polypeptide. The immobilized first antibody is incubated with a sample suspected of containing the polypeptide. If present, the polypeptide binds to the first antibody.

A second antibody, also specific for the polypeptide, binds to the immobilized polypeptide. The second antibody may be labeled by methods known in the art. Non-immobilized materials are washed away, and the presence of immobilized label indicates the presence of the polypeptide. This and other immunoassays are described by David, et al., in U.S. Pat. No. 4,376,110 assigned to Hybritech, Inc., La Jolla, Calif.

The probe may also be a nucleic acid molecule that recognizes a FrpB nucleic acid molecule of the invention. Methods for determining whether a nucleic acid molecule probe recognizes a specific nucleic acid molecule in a sample are known in the art. Generally, a labeled probe that is complementary to a nucleic acid sequence suspected of being in a sample is prepared. The presence of probe hybridized to the target nucleic acid molecule indicates the presence of the nucleic acid molecule. Suitable methods are described by Schneider et al in U.S. Pat. No. 4,882,269, which is assigned to Princeton University, and by Segev in PCT Application WO 90/01069, which is assigned to ImClone Systems Incorporated.

The probes described above are labeled in accordance with methods known in the art. Methods for labeling antibodies have been described, for example, by Hunter and Greenwood (93) and by David et al. (94). Additional methods for labeling antibodies have been described in U.S. Pat. Nos. 3,940,475 and 3,645,090. Methods for labeling oligonucleotide probes have been described, for example, by Leary et al (95); Renz and Kurz (96); Richardson and Gumport (97); Smith et al. (98); and Meinkoth and Wahl (99).

The label may be radioactive. Some examples of useful radioactive labels include $^{32}P$, $^{125}I$, $^{131}I$, and $^3H$. Use of radioactive labels have been described in U.K. 2,034,323, U.S. Pat. No. 4,358,535, and U.S. Pat. No. 4,302,204.

Some examples of non-radioactive labels include enzymes, chromophors, atoms and molecules detectable by electron microscopy, and metal ions detectable by their magnetic properties.

Some useful enzymatic labels include enzymes that cause a detectable change in a substrate. Some useful enzymes and their substrates include, for example, horseradish peroxidase (pyrogallol and o-phenylenediamine), beta-galactosidase (fluorescein beta-D-galactopyranoside), and alkaline phosphatase (5-bromo-4-chloro-3-indolyl phosphate/nitro blue tetrazolium). The use of enzymatic labels have been described in U.K. 2,019,404, EP 63,879, and by Rotman (100).

Useful chromophores include, for example, fluorescent, chemiluminescent, and bioluminescent molecules, as well as dyes. Some specific chromophores useful in the present invention include, for example, fluorescein, rhodamine, Texas red, phycoerythrin, umbelliferone, and luminol.

The labels may be conjugated to the antibody or nucleotide probe by methods that are well known in the art. The labels may be directly attached through a functional group on the probe. The probe either contains or can be caused to contain such a functional group. Some examples of suitable functional groups include, for example, amino, carboxyl, sulfhydryl, maleimide, isocyanate, isothiocyanate.

The label may also be conjugated to the probe by means of a ligand attached to the probe by a method described above and a receptor for that ligand attached to the label. Any of the known ligand-receptor combinations is suitable. The biotin-avidin combination is preferred.

The polypeptide of the invention may be used to detect the presence of antibodies specific for *N. gonorrhoeae* or *N. meningitidis* in a sample. The method comprises preparing a polypeptide containing a segment having an amino acid sequence that is substantially the same as a FrpB from either *N. gonorrhoeae* to detect antibodies to *N. gonorrhoeae* or *N. meningitidis* to detect antibodies to *N. meningitidis*. The polypeptide may be prepared as described above.

The sample may, for example, be from a patient suspected of being infected with *N. gonorrhoeae* or *N. meningitidis*. Suitable assays are known in the art, such as the standard ELISA protocol described by R. H. Kenneth (101).

Briefly, plates are coated with antigenic polypeptide at a concentration sufficient to bind detectable amounts of the antibody. After incubating the plates with the polypeptide, the plates are blocked with a suitable blocking agent, such as, for example, 10% normal goat serum. The sample, such as patient sera, is added and titered to determine the endpoint. Positive and negative controls are added simultaneously to quantitate the amount of relevant antibody present in the unknown samples. Following incubation, the samples are probed with goat anti-human Ig conjugated to a suitable enzyme. The presence of anti-polypeptide antibodies in the sample is indicated by the presence of the enzyme.

The following Examples section is set forth to aid in an understanding of the invention. This section is not intended to, and should not be construed to, limit in any way the invention as set forth in the claims which follow thereafter.

EXAMPLES

Strains and growth conditions. Bacterial strains used in this experiment are described in Table 1. Neisseria strains were routinely cultured on GCB media (Difco Laboratories) containing Kellogg's supplements I and II (29) and grown overnight at 35° C. in an atmosphere of 5%$CO_2$. Antibiotic selection employed chloramphenicol at 1 $\mu$g/ml for mTn3 (Cm)(51) mutagenized strains and streptomycin at 100 $\mu$g/ml for $\Omega$ (44) mutagenized strains.

For western blot analysis of total membrane proteins of iron-stressed gonococci, cells were grown in CDM as previously described (13). Cultures were made iron replete as indicated by the addition of 100 uM ferric citrate.

*E. coli* strains were routinely cultured on Luria-Bertani (LB) media (47). Antibiotic selection was 100 $\mu$g/ml ampicillin, 100 $\mu$g/ml streptomycin, 40 $\mu$g/ml kanamycin, and/or 30 $\mu$g/ml cholramphenicol. $\delta$-aminolevulinic acid was used at 30 $\mu$g/ml and heme at 50 $\mu$g/ml. *E. coli* cultures were iron stressed by the addition of 200 $\mu$M 2,2-diyridyl (Sigma Chemical Co., St. Louis, Mo.). Deferoxamine mesylate (desferal) was obtained from Ciba-Geigy (Basel, Switzerland).

SDS-PAGE and Western Blotting. SDS-PAGE was performed in 7.5% polyacrylamide resolving gel and 4.5% polyacrylamide stacking gel. Electrophoresis was carried out at either 40 mA for one gel, or 80 mA for two gels in the discontinuous buffer system of Laemmli (32). Transfer and development were as described previously (23,61).

Preparation of polyclonal antisera and monoclonal antibodies. Preparation of polyclonal antisera was described previously (8). Anti-FrpB monoclonal antibodies were generated by methods described previously (60).

DNA isolation, digestion, and Southern blot analysis. Chromosomal DNA was purified by CsCl-gradient centrifugation according to the methods of Stern et al. (54). Plasmids were purified by either CsCl centrifugation or according to the instructions provided in the MAGIC MINIPREP™ DNA Purification Kit (Promega; Madison Wis.). Southern blotting and DNA hybridizations were performed as previously described (13). Restriction enzymes, Klenow fragment of DNA polymerase I, and T4 DNA ligase were purchased from New England Biolabs (Beverly, Mass.) or Bethesda Research Laboratories (Gaithersburg, Md.) and were used according to the manufacturer's specifications. $\lambda$-ZapII and pBluescript II SK+ were obtained from Stratagene (La Jolla, Calif.).

DNA sequencing and sequence analysis. CsCI-purified pUNCH319 and pUNCH325 were used as templates for double-stranded DNA sequencing (31) using United States Biochemical Sequenase and the dideoxy chain termination procedure of Sanger et al. (48). Both dG- and dI-labeling reactions were carried out for all primers. Both strands of pUNCH319 were sequenced using vector-specific or insert-specific primers. Exonuclease III/Exo VII nested deletions (40) were generated from the Mlu end of pUNCH325 and vector-specific primers were used to sequence individual deletion clones. Internal primers were used to sequence gaps between clones as well as the opposite strand. DNA sequences were analyzed with the Genetics Computer Group software package (15) (University of Wisconsin).

Mutagenesis and gonococcal transformation. pHP45$\Omega$ (44) was used to insertionally inactivate frpB. pUNCH321 was digested with Bgl I and ends were repaired with Klenow. pHP45$\Omega$ was digested with Sma I and the 2.0 kb $\Omega$ fragment was isolated from an agarose gel according to the instructions provided in the Geneclean II® Kit (Bio101 Inc. La Jolla, Calif.). Transformation of plasmid DNA into FA19 was as previously described (7).

Preparation of FrpB for amino-terminal sequence analysis. N-lauroylsarcosine (Sigma) insoluble membrane fractions were prepared from iron-stressed gonococcal strain UU1008 and protein concentration was determined by a bicinchoninic acid assay (BCA) (Pierce, Rockford, Ill.). Two hundred micrograms of protein was loaded into a preparative well of a 7.5% SDS-polyacryamide gel, poured 24 hours previously to permit TEMED (N,N,N',N'-tetramethylethylenediamine) and APS (ammonium persulfate) to evaporate. Electrophoresis was carried out at 40 mA constant current using the discontinuous buffer system of Laemmli (32). The gel was soaked for 15 minutes in transfer buffer (13) before transferring. PVDF (polyvinylidene difluoride) membrane was placed in 100% methanol for two seconds, transferred to distilled deionized water (ddH$_2$O) for five minutes, and soaked in transfer buffer for 10 minutes prior to transfer. Transfer was for three and a half hours at 90 mA in a submerged trans-blot apparatus (BioRad, Richmond, Calif.). Subsequent to transfer, the PVDF membrane was stained for five minutes in 0.1% Coomassie Brilliant Blue, 20% methanol, and 10% acetic acid to visualize proteins and destained for 10 minutes in ddH2O with one change. Filter was frozen at −20° C. overnight. FrpB was identified by molecular weight and the amino-terminal amino acid sequence of the protein on the filter was determined by the Protein Microsequencing Facility at UCLA.

$^{55}$Fe uptake assays. Data were compiled from three individual experiments performed in triplicate on separate days. Gonococci were iron stressed as previously reported (2) prior to experimentation. SDS-PAGE and Western blotting of whole-cell lysates were routinely performed to determine that cultures were consistently and equivalently iron stressed, as evidenced by reactivity with anti-FrpB monoclonal antibody and/or anti-Tbp1 antisera. Iron-uptake assays were performed as previously reported (9) with the following modifications. Filters were blocked just prior to experimentation with 30 μl, 10 mg/ml BSA in 1×CDM. Assays were performed in 200 μl volumes in 96 well filtration plates (MAHV Millipore, Bedford, Mass.) at 35° C. in a 5% CO$_2$ atmosphere. Potassium cyanide was dissolved in 1×CDM. The vacuum manifold was from Millipore Multiscreen Assay System. Heme was used at 0.5 μM, transferrin at 6.25 μM, and citrate at 100 μM. Membranes were air dried overnight, and the Millipore punch kit was used to separate and collect individual filters prior to counting. Data were expressed as counts per minute per μg of protein.

Preparation of aerobactin and enterobactin. Purified aerobactin and enterobactin were the generous gift of P. E. Klebba. Aerobactin was ferrated as follows. Ferric sulfate was dissolved to 4 mM in 50 ml ddH$_2$O containing 1.5 μl HCl. 400μ 4 mM aerobactin was added to 400 μl 4 mM ferric sulfate and 80 μl 0.5M Na$_2$HPO$_4$. The ferri-aerobactin was run over a CM-cellulose (Sigma, St. Louis, Mo.) column equilibrated in 0.05M Na$_2$HPO$_4$. The final concentration of aerobactin was determined by reading the absorbance at 400 nM (24).

Iron sources. Human transferrin, human lactoferrin, bovine heme, human hemoglobin, and human haptoglobin were obtained from Sigma Chemical Co. (St. Louis, Mo.). $^{55}$Fe hemin was purchased from the custom synthesizing facility at NEN Products Dupont (Wilmington, Del.) lot number FE55.1193RS. Transferrin, lactoferrin, and citrate were ferrated with $^{55}$FeCl as previously described (36).

RNase assay. The RNase assay was performed as previously described (71), except 0.1N HCl was used instead of 0.5N HCl.

Hemin affinity purification. Hemin agarose was purchased from Sigma Chemical Co. (St. Louis, Mo.). The method of affinity purification was described by Lee (33).

Bactericidal assays. Bactericidal assays were performed as described previously (18).

Cloning the gonococcal frpB gene. Sarcosyl insoluble membrane fractions from gonococcal strain UU1008 were used to obtain FrpB N-terminal amino acid sequence (see above). A degenerate oligonucleotide containing inosine (designated MB.3) was deduced from this sequence and used to probe a Southern blot of FA19 chromosomal DNA. Each restriction digest contained a single hybridizing band. A 5.8 kb Dra I fragment was chosen for further analysis.

A λ-ZapII library containing EcoRI-linkered FA19 chromosomal Dra I fragments (2) was screened with oligo MB.3. Approximately one positive plaque was identified for every 10,000 plaques screened. Attempts to excise the phagemid containing the intact insert consistently resulted in deletion products smaller than pBluescript II SK$^+$ alone. Since such a large chromosomal fragment potentially contained both the frpB promoter and entire frpB coding sequence and that the expression of FrpB might be toxic in *E. coli*, smaller fragments were subcloned into pBluescript II SK$^+$.

DNA prepared from one of the positively hybridized plaques, λfrpB-4, was digested with EcoRI to release the insert DNA. The expected 5.8 kb fragment was isolated from an agarose gel and further digested with Cla I to generate a 540 bp, MB.3-hybridizing fragment and an approximately 5.3 kb fragment which did not hybridize to MB.3. The smaller fragment ligated into pBluescript II SK$^+$ was stable in *E. coli* DH5αMCR and was designated pUNCH319. The larger fragment ligated into pBluescript II SK$^+$ generated pUNCH320. pUNCH320 caused *E. coli* DH5αMCR to grow poorly and appeared to be severely restricted in copy number. These data suggested that other sequences located 3' of frpB may also be toxic to *E. coli* and that further subcloning was necessary to obtain stable clones. Digestion of pUNCH320 with Mlu I and EcoR I released fragments of approximately 1.0 kb and 1.5 kb, leaving a 2.8 kb Cla I-Mlu I fragment attached to pBluescript II SK$^+$. This 5.8 kb fragment (vector plus 2.8 kb Cla I-Mlu I insert) was subsequently isolated, treated with Klenow, and re-ligated to itself to generate pUNCH325. DH5αMCR (pUNCH325) transformants were stable and the plasmid copy number apparently normal.

Nucleotide sequence and analysis of frpB. PCR amplification of chromosomal DNA followed by sequence analysis of clones confirmed the Cla I junction between pUNCH319 and pUNCH325. The combined nucleotide sequence and deduced amino acid sequence from pUNCH319 and pUNCH325 are shown in SEQ ID No: 1 Putative promoter sequences were located upstream of a well conserved Fur box (4). A string of nine cytosine residues was noted between the putative −10 and −35 RNA-polymerase binding sites. A Shine-Dalgarno sequence starting at nucleotide 307 and ending at nucleotide 310, was located six bases before an ATG codon, the start of a 1,925 bp open reading frame (ORF). This ORF encoded a protein of 713 amino acids. The predicted protein contained a typical signal sequence and characteristic Ala-X-Ala, signal peptidase I cleavage site. The first ten amino acids adjacent to the cleavage site were identical to the peptide sequence obtained from the mature FrpB protein. A classical TonB box was noted at residues 32–36. The mature protein had a calculated molecular weight of 76.6 kD and an isoeletric point of 10.38. The sequence downstream of the ORF revealed an inverted repeat but no string of T residues characteristic of rho-independent transcription termination (69). The protein terminated with an aromatic residue preceded by nine alternating hydrophobic and hydrophilic amino acids. This structure is typical of many bacterial outer membrane proteins sequenced to date (58).

GenBank homologies. Comparison of FrpB with other sequences in GenBank revealed some interesting homologies. Several regions of the predicted FrpB protein shared similarity with regions identified in other proteins as potentially important for membrane localization and/or TonB interaction. Localized homology was found between FrpB and the family of TonB-dependent outer membrane receptor proteins including BtuB (25) and FepA (35) of *E. coli* and between Tbp1 (13) and IroA (42) of Neisseria species. This similarity was limited to the highly conserved domains (13), and suggested that FrpB may also be a TonB-dependent receptor. More similarity was found with HemR, the hemin receptor of *Yersinia enterocolitica* (55). HemR is an iron-regulated, outer membrane protein that is also a member of the family of TonB-dependent receptor proteins. Overall the two proteins were 26% identical and 48% similar. The most notable similarity was seen with CopB, a major outer membrane protein of *Moraxella catarrhalis* (26). Overall FrpB and CopB were 52% identical and 71% similar.

Transposon mutagenesis of frpB. In order to construct FrpB mutants, the gonococcal insert in pUNCH319 was ligated into pUP1 (19), creating pUNCH321. The Ω fragment from pHP45Ω was ligated into a unique Bgl I site in pUNCH321 (SEQ ID No: 1). This DNA was reintroduced into the chromosome of gonococcal strain FA19 by transformation and allelic replacement, creating FA6807. Southern blot analysis of chromosomal DNA from FA19 and FA6807 indicated that a 450 bp, MB.3-hybridizing, HincII fragment present in the parent was missing in FA6807 and a new reactive band of approximately 2.5 kb was present. An identical blot probed with Ω, only hybridized to the 2.5 kb fragment in FA6807. SDS-polyacrylamide gel electrophoresis (SDS-PAGE) and Western blot analysis with anti-FrpB monoclonal antibody W.6, confirmed that FrpB was absent from this strain.

The Ω insertion in frpB was also introduced into FA6747 (tbpA::mTn3(Cm)) by transformation and allelic replacement creating FA6808. The FrpB⁻/Tbp1⁻ phenotype of FA6808 was confirmed by SDS-PAGE and Western blot analysis. This strain was used for FrpB function analysis as described below.

Utilization of iron sources. In an attempt to determine the function that FrpB plays in iron utilization, FA19 and FA6807 were grown in chemically-defined media (CDM) lacking iron. Aliquots of iron-stressed cultures were plated onto CDM agarose containing 10 $\mu$M Desferal and GC base agar containing 50 $\mu$M Desferal. Sterile 3 mm discs containing either citrate, transferrin, lactoferrin, heme, hemoglobin, or hemoglobin bound to haptoglobin were positioned around each plate. One disc without any added iron source was added as a negative control. After overnight incubation, growth of both strains was evident around all discs except the negative control.

*N. gonorrhoeae* can utilize aerobactin (67) and enterobactin (45) as iron sources. To determine if FrpB functioned as either an aerobactin or enterobactin receptor, FA19, FA6808, FA6747, KDF541, KDF541/pABN6, and BN1071 (Table 1) were iron stressed in CDM as above and plated onto CDM agarose containing 2.5 $\mu$M, 30% iron-saturated transferrin. FA6747 and FA6808 could not use Tf as an iron source because they lacked Tbp1, therefore these strains could grow only in the presence of a functional high-affinity siderophore receptor. Three sterile discs were positioned around each plate. Either 30% saturated lactoferrin (positive control for gonococcal viability) or filter-sterilized, iron-free supernatant from LG1315 pCoIV (aerobactin producer) or AN102 (enterobactin hyper-producer) were added to each disk. After overnight incubation, *E. coli* controls grew as expected suggesting that both siderophores were efficient at stripping iron from transferrin, the sole iron source provided in the media. FA19 grew over the entire transferrin plate as expected, however, growth of FA6808 and FA6747 was only evident around the lactoferrin disks, suggesting that the cells were viable but unable to use aerobactin or enterobactin under these conditions.

Aerobactin utilization by FA19 and FA6807 was further evaluated in chemically-defined, liquid media, employing various concentrations of purified ferri-aerobactin. The aerobactin receptor-negative *E. coli* strain KDF541 and aerobactin receptor-positive *E. coli* strain KDF541 (pABN6) were used as controls. These data suggested that *N. gonorrhoeae* FA19 and FA6807 used ferri-aerobactin similarly and in a concentration-dependent fashion analogous to the aerobactin receptor-negative *E. coli* control. Growth stimulation of gonococci by ferri-aerobactin required relatively high concentrations (3 $\mu$M) and never attained a density equivalent to that of the Tf or citrate controls. These experiments confirmed the ability of gonococci to utilize ferri-aerobactin as an iron source in vitro but showed that this ability was not dependent upon a high-affinity receptor-mediated event.

$^{55}$Fe uptake from hemin, Tf, and citrate. Because of the high degree of similarity between HemR, a known hemin receptor in *Y. enterocolitica* and FrpB, it was analyzed whether a quantitative difference in $^{55}$Fe uptake from hemin could be detected between FA19 and FA6807. Uptake of $^{55}$Fe from transferrin by FA19, FA6807, and the Tbp1 mutant FA6747 were used as controls. The results indicated that while $^{55}$Fe uptake from transferrin was approximately wild type in FA6807(P=0.826), $^{55}$Fe uptake from hemin was reduced by approximately 60% (P<0.001). Surprisingly, $^{55}$Fe uptake from hemin was also significantly reduced in FA6747 (P<0.001). To determine whether the inability to use $^{55}$Fe from hem in was specific to FA6807(FrpB⁻) and FA6747 (Tbp1⁻¹), $^{55}$Fe uptake from hemin was assayed in other well-characterized, gonococcal mutants specifically altered in the expression of other iron-repressible proteins. The Tbp2⁻ and Lbp⁻ strains, FA6819 and FA6775 respectively, were also reduced in $^{55}$Fe internalization from hemin (P<0.001). These data suggested that either more than one protein was involved in the internalization of hemin iron or the notable decrease in hemin-iron uptake in these mutants resulted from unanticipated, non-specific effects of each of these mutations on a separate membrane-bound, heme-iron-uptake system.

Reconstruction of frpb in pACYC184 and functional complementation of RK1065(hemA). In an attempt to determine if FrpB could function as a heme receptor, an *E. coli* hemA mutant was complemented with FrpB. Although expression of FrpB from the high copy-number vector pBluescript II SK⁺ was toxic to *E. coli*, expression from the low copy-number vector pACYC184 was tolerated. Briefly, the insert from pUNCH319 was ligated into the Cla I and BamH I sites of pACYC184, generating pUNCH330. pUNCH330 was digested with Cla I and the gel-purified Cla I-Xba I fragment from pUNCH325 was ligated into this site as follows. After ligating for four hours, Klenow was added to the ligation mixture for 30 minutes at room temperature to repair non-ligated Cla I and Xba I ends. The reaction was further ligated overnight. The frpB clone in pACYC184 was designated pUNCH331. FrpB expression from pUNCH331 was iron repressible, suggesting regulation by *E. coli* Fur.

RK1065 is an *E. coli* hemA mutant which is unable to synthesize or internalize heme (27). Growth stimulation requires either δ-aminolevulinic acid, or heme and a functional heme receptor. Transformation of pUNCH331 into RK1065 supported growth on heme plates, whereas pACYC184 alone did not. An Rnase leakage assay was performed to determine if FrpB expression altered the *E. coli* outer membrane, thereby allowing heme to simply diffuse into the cell (71). The *E. coli* strains C386 and HB101 containing pEBH21 were used as positive and negative controls respectively. No difference in leakiness was detected between RK1065 (pACYC184) and RK1065 (pUNCH331), suggesting that growth of RK1065 (pUNCH331) on heme plates was not due to a membrane perturbation gross enough to permit leakage of the periplasmic protein RNase H. Nevertheless, RK1065 (pUNCH331) was more sensitive to several hydrophobic antibiotics than the same strain with pACYC194 alone. This experiment suggested that the presence of FrpB in *E. coli* probably allowed heme to enter non-specifically either by creating a pore or by perturbing the integrity of the outer membrane. Uptake of $^{55}$Fe from hemin in RK1065 (pUNCH331) was not inhibited by KCN, consistent with a non-specific, non-receptor mediated mechanism of uptake.

Bactericidal Assay. In *M. catarrhalis*, CopB, the protein with the greatest similarity to FrpB, appears to play a major role in serum resistance. Mutants which are missing CopB have decreased serum resistance. Mutants which are missing CopB have decreased serum resistance and survival in a mouse model (26). Standard bactericidal assays were performed with normal human serum on FA19 and FA6807 grown under iron-limiting conditions and were unable to detect any difference in survival; both strains were completely serum resistant.

TABLE 1

Bacterial strains, plasmids and phage.

| Strain, plasmid or phage | Description | Source/reference |
| --- | --- | --- |
| FA19 | Wild type | [Mickelsen, 1981 #38] |
| FA6807 | frpB::Ω(FrpB$^-$) | This study |
| FA6808 | frpB::Ω tbpA::mTn3(Cm) (FrpB$^-$, Tbp1$^-$) | This study |
| FA6747 | tbpA::mTn3(Cm) (Tbp1$^-$) | [Cornelissen, 1992 #13] |
| FA6819 | ΔtbpB (Tbp2$^-$) | [Anderson, 1994 #2] |
| FA6775 | lbpA::mTn3(Cm) (Lbp$^-$) | [Biswas, 1994 #6] |
| UU1008 | Wild type | Zell McGee |
| DH5αMCR | F$^-$ mcrA mcrB mrr φ80dlacZΔM15 Δ(argF-lac)U169 recA1 endA1 hsdR hsdM supE44 λ$^-$thi-1 gyrA96 relA1 | Bethesda Research Labs |
| BN1071 | F$^-$, pro, trp, rslL, entA (Ent$^-$, FepA$^+$) | [Klebba, 1982 #30] |
| AN102 | BN1071, lue, fepA (Ent$^+$, FepA$^-$) | [Klebba, 1982 #30] |
| KDF541 | BN1071, entA, fepA (Ent$^-$, FepA$^-$) | [Rutz, 1992 #46] |
| KDF541/pABN6 | (Ent$^-$, FepA$^-$, IutA$^+$, luc$^-$) | [de Lorenzo, 1987] |
| LG1315/pcoIV | BN1071, cir (IutA$^+$, luc$^+$) | [Warner, 1981 #63] |
| RK1065 | hemA | R. Kadner |
| HB101 | F$^-$, hsd20 (r$_B^-$, m$_B^-$), recA13, ara-14, proA2, lacY1, galK2, rpsL20 (Sm$^r$), xyl-5, mtl-1, supE44, λ$^-$ | Maniatis et.al. 1982 |
| C386 | ompA lpp | [Sonntag, 1978 #53] |
| pACYC184 | ori p15a, Cm$^R$, Tc$^R$ | New England Biolabs |
| pBluescript II SK+ | ori pMB1, Ap$^R$ | Stragene |
| pHP45Ω | source for the Ω fragment (Sm$^R$) | [Prentki, 1984 #44] |
| pUP1 | pHSS6 containing gonococcal uptake sequence (Kan$^R$) | [Elkins, 1991 #19] |
| pUNCH319 | pBluescript II SK$^+$ containing 540 bp EcoR I-Cla I fragment from λfrpB.4 | This Study |
| pUNCH320 | pBluescript II SK$^+$ containing 5.3 kb Cla I-EcoRI fragment from λfrpB.4 | This Study |
| pUNCH321 | pUP1 containing 540 bp EcoR I-Cla fragment from pUNCH319 | This Study |
| pUNCH324 | pUNCH321 containing Ω fragment from pHP45Ω in unique Bgl I site | This Study |
| pUNCH325 | pBluescript II SK$^+$ containing 2.8 kb Cla I-Mlu I fragment from pUNCH320 | This Study |
| pUNCH330 | 540 bp EcoR I-Cla fragment from pUNCH319 in pACYC184 | This Study |
| pUNCH331 | reassembled gonococcal frpB gene in pACYC184 | This Study |
| λ ZapII | excisable lambda phage vector | Statagene |

REFERENCES

1. Ala' Aldeen, D. A., H. A. Davies, and S. P. Borriello. 1994. Vaccine potential of meningococcal FrpB: studies on surface exposure and functional attributes of common epitopes. Vaccine 12:535–541.

2. Anderson, J. E., P. F. Sparling and C. N. Cornelissen. 1994. Gonococcal transferrin-binding protein 2 facilitates but is not essential for transferrin utilization. J. Bacteriol. 176.

3. Archibald, F. S., and I. W. DeVoe. 1980. Iron acquisition by *Neisseria meningitidis* in vitro. Infect. Immun. 27: 322–334.

4. Bagg, A. and J. B. Neilands. 1987. Molecular mechanism of regulation of siderophore-mediated iron assimilation. Microbiol. Rev. 51:509–518.

5. Berish, S. A., S. Subbarao, C. Y. Chen, D. L. Trees, and S. A. Morse. 1993. Identification and cloning of a fur homolog from *Neisseria gonorrhoeae*. Infect. Immun 61:4599–4606.

6. Biswas, G. and P. F. Sparling. 1995. Characterization IbpA, the structural gene for a loctoferrin receptor in *Neisseria gonorrhoeae*. Infection and Immunity 63 (8): 2958–2967.

7. Biswas, G. D., J. Graves, R. Schwalbe, and P. F. Sparling. 1986. Construction of isogenic gonococcal strains varying in the presence of a 4.2-kilobase cryptic plasmid. J. Bacterial. 167: 685–694.

8. Black, J. R., D. W. Dyer, M. K. Thompson, and P. F. Sparling. 1986. Human immune response to iron-repressible outer membrane proteins of *Neisseria meningitidis*. Infect. Immun. 54:710–713.

9. Blanton, K. J., G. D. Biswas, J. Tsai, J. Adams, D. W. Dyer, S. M. Davies, G. G. Koch, P. K. Sen, and P. F. Sparling. 1990. Genetic evidence that *Neisseria gonorrhoeae* produces specific receptors for transferrin and lactoferrin. J. Bacteriol. 172:5225–5235.

10. Briat. J. F. 1992. Iron Assimilation and Storage in Prokaryotes. J. Gen. Microbiol. 138:2475–2483.

11. Brock, J. H., P. H. Williams, J. Liceaga, and K. G. Wooldridge. 1991. Relative Availability of Transferrin-Bound Iron and Cell Derived Iron to Aerobactin-Producing and Enterochelin-Producing Strains of *Escherichia coli* and to Other Microorganisms. Infect. Immun. 59:3185–3190.

12. Brook, I. 1994. The role of encapsulated anaerobic bacteria in synergistic infections. FEMS Mircobiol. Rev. 13:65–74.

13. Cornelissen, C. N., G. D. Biswas, J. Tsai, D. K. Paruchuri, S. A. Thompson, and P. F. Sparling. 1992. Gonococcal transferrin-binding protein 1 is required for transferrin utilization and is homologous to TonB-dependent outer membrane receptors. J. Bacteriol. 174:5788–5797.

14. de Lorenzo, V., S. Wee, M. Herrero, and J. B. Neilands. 1987. Operator sequences of the aerobactin operon of plasmid ColV-K30 Binding the ferric uptake regulation (fur) repressor. J. Bacteriol. 169:2624–2630.

15. Devereux, J., P. Haeberli, and O. Smithies. 1984. A comprehensive set of sequence analysis programs for the VAX. Nucleic Acids Res. 12:387–395.

16. Dyer, D. W., E. P. West, W. McKenna, S. A. Thompson, and P. F. Sparling. 1988. A pleiotrophic iron-uptake mutant of *Neisseria meningitidis* lacks a 70-kilodalton iron-regulated protein. Infect. Immun. 56:977–983.

17. Dyer, D. W., E. P. West, and P. F. Sparling. 1987. Effects of serum carrier proteins on the growth of pathogenic Neisseriae with hem-bound iron. Infect. Immun. 55:2171–2175.

18. Elkins, C., N. H. Carbonetti, V. A. Varela, D. Stirewalt, D. G. Klapper, and P. F. Sparling. 1992. Antibodies to N-terminal peptides of gonococcal porin are bactericidal when gonococcal lipopolysaccharide is not sialylated. Mol. Microbiol. 6:2617–2628.

19. Elkins, C., C. E. Thomas, H. S. Seifert, and P. F. Sparling. 1991. Species-specific uptake of DNA by gonococci is mediated by a 10-base pair sequence J. Bacteriol. 173:3911–3913.

20. Finlay, B. B., and S. Falkow. 1989. Common themes in microbial pathogenecity. Microbiol. Rev. 53:210–230.

21. Gothschlich, E. C., C. Cornelissen, S. A. Hill, J. M. Kooney, C. Marschal, S. A. Morse, S. Normak, A. B. Schryvers, H. S. Siefert, P. F. Sparling, and J. Swanson. The mechanism of genetic variation of gonococcal pili. Iron-inducible proteins of Neisseria. A consensus. In *Neisseriae 1990: Proceeding of the Seventh International Conference on Pathogenic Neisseria*. Achtman, M. 1991. Berlin, Federal Republic of Germany: Walter de Gruyer.

22. Hardham, J. M., and L. V. Stamm. 1994. Identification and characterization of the Treponema pallidum tpn50 gene, an ompA homolog. Infect. Immun. 62: 1015–1025.

23. Harlow, E., and D. Lane, 1988. p. 471–510. In Antibodies: a laboratory manual, Cold Spring Harbor, Cold Spring Harbor, N.Y.

24. Harris, W. R., C. J. Carrano, and K. N. Raymond. 1979. Coordination chemistry of microbial compounds. 16. Isolation, characterization, and formation constants of ferric aerobactin J. Am. Chem. Soc. 101: 2722–2727.

25. Heller, K. J., R. J. Kadner, and K. Gunther. 1988. Suppression of the btuB451 mutation by mutations in the tonB gene suggests a direct interaction between TonB and TonB-dependent receptor proteins in the outer membrane of *Escherichia coli*. Gene 64: 147–53.

26. Helminen, M. E., I. Maciver, M. Paris, J. L. Latimer, S. L. Lumbley, L. D. Cope, G. H. McCracken, and E. J. Hansen. 1993. A mutation affecting expression of a major outer membrane protein of *Moraxella catarrhalis* alters serum resistance and survival of this organism in vivo. J. Infect. Dis. 168:1194–1201.

27. Henderson, D. P., and S. M. Payne. 1993. Cloning and characterization of the *Vibrio cholerae* genes encoding the utilization of iron from haemin and haemoglobin. Mol. Microbiol. 7:461–469.

28. Jann, K., and B. Jann. 1992. Capsules of *Escherichia coli*, expression and biological significance. Can. J. Microbiol. 38:705–710.

29. Kellog, D. S., Jr., W. L. Peacock Jr., W. E. Deacon, L. Brown, and C. I. Pirkle. 1963. *Neisseria gonorrhoeae*. I. Virulence genetically linked to clonal variation. J. Bacteriol. 85:1274–1279.

30. Klebba, P. E., M. A. Mcintosh, and J. B. Neilands. 1982. Kinetics of biosynthesis of iron-regulated membrane protein in *Escherichia coli*. J. Bacteriol. 149:880–888.

31. Kraft, R. J. Tardiff, K. S. Krauter, and L. A. Leinwand. 1988. Using mini-prep plasmid DNA for sequencing double stranded templates with Sequenase. Biotechniques. 6:544–546.

32. Laemmli, U. K. 1970. Cleavage of structural proteins during the assembly of the head of bacteriophage T4. Nature (London). 227:680–685.

33. Lee, B. C. 1992. Isolation of haemin-binding proteins of *Neisseria gonorrhoeae*. J. Med. Microbiol. 36:121–127.

34. Levinson, G, and G. A. Gutman. 1987. Slipped-stranded mispairing: a major mechanism for DNA sequence evolution. Mol. Biol.Evol. 4:203–221.

35. Lundrigan, M. D., and R. J. Kadner. 1986. Nucleotide sequence of the gene for the ferrienterochelin receptor FepA in *Escherichia coli*. Homology among outer membrane receptors that interact with TonB. J. Biol Chem. 261:10797–10801.

36. McKenna, W. R., P. A. Mickelsen, P. F. Sparling, and D. W. Dyer. 1988. Iron uptake from lactoferrin and transferrin by *Neisseria gonorrhoeae*. Infect. Immun. 56:785–791.

37. Meyer, T. 1987. Molecular basis of surface antigenic variation in Neisseria Trends in Genet. 3:319–324.

38. Mickelsen, P. A., and P. F. Sparling. 1981. Ability of *Neisseria gonorrhoeae, Neisseria meningitidis*, and commensal Neisseria species to obtain iron from transferrin and iron compounds. Infect. Immun. 33:555–564.

39. Neilands, J. B. 1981. Microbial iron compounds. Annu. Rev. Biocheml. 50:715–731.

40. Ozkaynak, E., and S. D. Putney. 1987. A unidirectional deletion technique for the generation of clones for sequencing. Biotechniques. 5:770–773.

41. Pettersson, A., B. Kuipers, M. Pelzer, E. Verhagen, R. H. Tiesjema, J. Tommassen, and J. T. Poolman. 1990. Monoclonal antibodies against the 70-kilodalton iron-regulated protein of *Neisseria meningitidis* are bactericidal and strain specific. Infect Immun. 58:3036–41.

42. Pettersson, A., d. L. P. van J. T. Poolman, and J. Tommassen. 1993. Molecular characterization of the 98-kilodalton iron-regulated outer membrane protein of *Neisseria meningitidis*. Infect Immun. 61:4724–33.

43. Postle, K. 1990. TonB and the gram-negative dilemma. Mol Microbiol. 4:2019–25.

44. Prentki, P., and H. M. Krisch. 1984. In vitro insertional mutagenesis with a selectable DNA fragment. Gene. 29:303–313.

45. Rutz, J. M., T. Abdullah, S. P. Singh, V. I. Kalve, and P. E. Klebba. 1991. Evolution of the ferric enterobactin receptor in gram-negative bacteria. J. Bacteriol. 173:5964–5974.

46. Rutz, J. M., J. Liu, J. A. Lyons, J. Goranson, S. K. Armstrong, M. A. McIntosh, J. B. Feix, and P. E. Klebba. 1992. Formation of a gated channel by a ligand-specific transport protein in the bacterial outer membrane. Science. 258:471–5.

47. Sambrook, J., E. F. Fritsch, and T. Maniatis. 1989. *Molecular Cloning: A Laboratory Manual.*, Cold Spring Harbor, N.Y.: Cold Spring Harbor Laboratory Press.

48. Sanger, F., S. Nicklen, and A. R. Coulson. 1977. DNA Sequencing with Chain Terminating Inhibitors. Proc. Natl. Acad. Sci. USA. .74:5463–5467.

49. Sarkari, J., N. Pandit, E. R. Moxon, and M. Achtman. 1994. Variable expression of the Opc outer membrane protein in *Neisseria meningitidis* is caused by size variation of a promoter containing poly-cytidine. Mol. Microbiol. 13:207–217.

50. Schryvers, A. B. 1989. Identification of the transferrin-and lactoferrin-binding proteins in *Haemophilus influenzae*. J. Med. Microbiol. 29:121–130.

51. Seifert, H. S., E. Y. Chen, M. So, and F. Heffron. 1986. Shuttle mutagenesis: A method of transposon Mutagenesis for *Sachharomyces cerevisiae*. Proc. Natl. Acad. Sci. USA. 83:735–739.

52. Smith, H. 1991. The influence of the host on mirobes that cause disease. Proc. R. Soc. Lond. B Biol. Sci. 246:97–105.

53. Sonntag, I., H. Schwarz, Y. Hirota, and U. Henning. 1978. Cell envelope and of *Escherichia coli*: multiple mutants missing the outer membrane lipoprotein and other major outer membrane proteins. J. Bacteriol. 136:280–285.

54. Stern, A., P. Nickel, T. F. Meyer, and M. So. 1984. Opacity determinants of *Neisseria gonorrhoeae*: gene expression and chromosomal linkage to the *Gonococcal pilus* gene. Cell 37:447–456.

55. Stojiljkovic, I., and K. Hantke. 1992. Hemin uptake systems of *Yersina enterococlitica*: similarities with other TonB-dependent systems in gram-negative bacteria. The EMBP Journal. 11:4359–4367.

56. Stojiljkovic, I., and K. Hantke. 1994. Transport of hemin across the cytoplasmic membrane thorough a hemin-specific, periplasmic-binding-protein-dependent transport system in *Yersinia enterocolitica*, Mol. Microbiol. in press.

57. Streisinger, G., and J. E. Owen. 1985. Mechanisms of spontaneous and induced frameshift mutations in bacteriophage T4. Genetics. 109:633–659.

58. Stuyve, M., M. Moons, and J. Tommassen. 1991. Carboxy-terminal pheylanin is essential for the correct assembly of a bacterial outer membrane protein. J. Mol. Biol. 218:141–148.

59. Thomas, C. E., and P. F. Sparling. 1994 Identification and cloning of a fur homologue from *Neisseria meningitidis*. Mol. Microbiol. 11:725–737.

60. Thompson, S. A., Wang, L. L., West, A., and Sparling P. F. 1993. *Neisseria meningitidis* Produces Iron-Regulated Proteins Related to the RTX Family of Exoproteins. J. Bacteriol. 175:811–818.

61. Towbin, J., T. Staehelin, and J. Gordon. 1979. Electrophoretic transfer of proteins from plyacrylamide gels to nitrocellulose sheets: procedures and some applications. Proc. Nat. Acad. Sci. USA. 76:4350–4354.

62. van Ham, S. M., L. van Alphen, and F. Mooi. 1993. Phase variation of *H. influenzae* fimbriae: transcriptional control of two divergent genes through a variable combine promoter region. Cell. 73:1187–1196.

63. Warner, P. J., P. H. Williams, A. Binderreif, and J. B. Neilands. 1981. Colv plasmid-specified aerobactin synthesis by invasive strains of *Escherichia coli*. Infect. Immun. 33:540–545.

64. Weinberg, E. D. 1978. Iron and infection. Microbiol. Rev. 42:45–66.

65. Weinberg. E. D. 1984. Iron withholding: a defense against infection and neoplasia. Physiol. Rev. 64:65–102.

66. West, S. E. H., and P. F. Sparling. 1985. Response of *Neisseria gonorrhoeae* to iron limitation: Alterations in expression of membrane proteins without apparent siderphore production. Infect. Immun. 47:388–394.

67. West, S. E. H., and P. F. Sparling. 1987. Aerobactin utilization by *Neisseria gonorrhoeae* and cloning a genomic DNA fragment that complements *Escherichia coli* fhuB mutations. J. Bacteriol. 169:3414–3421.

68. Willems, R., A. Paul, H. G. J. van der Heide, A. R. ter Avest, and F. R. Mooi. 1990. Fimbrial phase variation in *Bordetella pertussis*: a novel mechanism for transcriptional regulation. The EMBO Journal. 9:2803–2809.

69. Yager, T. D., and P. H. von Hippel, 1987. Transcription elongation and termination in *Escherichia coli*, p. 1241–1275. In F. C. Neidhardt, J. L. Ingraham, K. B. Low, B. Magasanik, M. Schaechter, and H. E. Umbarger, (ed), *Escherichia coli* and *Salmonella typhimurium*: cellular and molecular biology., American Society of Microbiology, Washington, D.C.

70. Yogev, D., R. Rosengarten, R. Watson-McKown, and K. S. Wise. 1991. Molecular basis of Mycoplasma surface surface antigenic variation: a novel set of divergent genes undergo spontaneous mutation of periodic coding regions and 5' regulatory sequences. The EMBO Journal. 10-4069–4079.

71. Young, K., and L. L. Silver. 1991. Leakage of periplasmic enzymes from envA1 strains of *Escherichia coli*. J. Bacteriol. 173:3609–3614.

72. Salfeld et al. J. Virol. 63, 798–808 (1989).

73. Isola et al. J. Virol. 63, 2325–2334 (1989).

74. Pearson and Lipman (74), Proc. Natl. Acad. Sci. USA 85:2444–2448 (1988).

75. West and Sparling (75) in Infect. Immun. 47, 388–394 (1985).

76. Schryvers and Morris (76) in Infect. Immun. 56,1144–1149 (1988).

77. Jones et al. in Finby, Solubilization and Reconstitution of Membrane Proteins: A Practical Approach, IRL Press (1986).

78. Helenius et al. in Biochim. Biophys. Acta 415, 29 (1975).

79. Hjelmeland and Chrambach, Methods Enzymol. 104, 305 (1984).

80. Methods Enzymol. 182 (Guide to Protein Chemistry, Deutscher, Ed. Section VII) 309 (1990).

81. Scopes, Protein Purification. Springer-Verlag, New York (1987).

82. Sambrook et al. "Molecular Cloning," Second Edition, Cold Spring Harbor Laboratory Press (1987).

83. Dieckmann and Tzagoloff in J. Biol. Chem. 260, 1513–1520 (1985).

84. Gene 67, 31 (1988).

85. Peptide Research 3, 167 (1990).

86. P. J. Southern and P. Berg, J. Mol. Appl. Genet. 1, 327–341 (1982).

87. S. Subramani et al, Mol. Cell. Biol. 1, 854–864 (1981).

88. R. J. Kaufmann and P. A. Sharp, J. Mol. Biol. 159, 601–621 (1982).

89. S. I. Scahill et al, Proc. Natl. Acad. Sci. USA 80, 4654–4659 (1983).

90. G. Urlaub and L. A. Chasin, Proc. Natl. Acad. Sci. USA 77, 4216–4220, (1980).

91. Kohler and Milstein, Nature 256, 495–497 (1975).

92. Huse et al., Science 246, 1275–1281 (1989).

93. Hunter and Greenwood, Nature 144, 945 (1962).

94. David et al., Biochemistry 13, 1014–1021 (1974).

95. Leary et al, Proc. Natl. Acad. Sci. USA (1983) 80:4045.

96. Renz and Kurz, Nucl. Acids Res. (1984) 12:3435.

97. Richardson and Gumport, Nucl. Acids Res. (1983) 11:6167.

98. Smith et al, Nucl. Acids Res. (1985) 13:2399.

99. Meinkoth and Wahl, Anal. Biochem. (1984) 138:267.

100. Rotman, Proc. Natl. Acad. Sci., 47, 1981–1991 (1961).

101. R. H. Kenneth, "Enzyme-Linked Antibody Assay with Cells Attached to Polyvinyl Chloride Plates" in Kenneth et al, *Monoclonal Antibodies*, Plenum Press, New York, page 376 (1981).

---

What is claimed is:

1. An isolated nucleic acid molecule comprising the nucleotide sequence of SEQ ID NO: 1 that encodes a FrpB protein.

2. An isolated nucleic acid molecule comprising the nucleotide sequence of SEQ ID NO: 3 that encodes a FrpB protein.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 2600 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 318..2456

(xi) SEQUENCE DESCRIPTION: SEQ ID NO:1:

```
AAACCGGTAC GGCGTTGCCC CGCCTTAGCT CAAAGAGAAC GATTCCCTAA GGTGCTGAAG      60

CACCGAGTGA ATCGGTTCCG TACTATTTGT ACTGTCTGCG GCTTCGCCGC CTTGTCCTGA     120

TTTTTGTTAG TCCACATATA CATTTCCGAC AAAACCTGTC AACAAAAAAC AACGCTTCGC     180

AAATAAAAAC GATAATCAGC TTTACACAAC CCCCCCCCGC TAATATAAAC AAAAATAATT     240

ATTATTATTT TTTCTTATCC TGCCAAACCT TAACGGTTTG GCTTAACTTC CCTTCATACA     300

CTCAAAAGGA CGAACAA ATG AAC GCC CCG TTT TTC CGC CTC AGC CTG CTC       350
                   Met Asn Ala Pro Phe Phe Arg Leu Ser Leu Leu
                     1               5                  10

TCG CTC ACA CTT GCC GCC GGC TTT GCC CAC GCG GCA GAA AAT AAT GCC      398
Ser Leu Thr Leu Ala Ala Gly Phe Ala His Ala Ala Glu Asn Asn Ala
             15                  20                  25

AAT GTC GCA TTG GAT ACC GTT ACC GTA AAA GGC GAC CGC CAA GGC AGC      446
Asn Val Ala Leu Asp Thr Val Thr Val Lys Gly Asp Arg Gln Gly Ser
         30                  35                  40

AAA ATC CGT ACC AAC ATC GTT ACG CTT CAA CAA AAA GAC GAA AGC ACC      494
Lys Ile Arg Thr Asn Ile Val Thr Leu Gln Gln Lys Asp Glu Ser Thr
```

```
                45                      50                      55
GCA ACC GAT ATG CGC GAA CTC TTA AAA GAA GAG CCC TCC ATC GAT TTC        542
Ala Thr Asp Met Arg Glu Leu Leu Lys Glu Glu Pro Ser Ile Asp Phe
 60                  65                  70                  75

GGC GGC GGC AAC GGC ACG TCC CAA TTC CTG ACG CTG CGC GGT ATG GGT        590
Gly Gly Gly Asn Gly Thr Ser Gln Phe Leu Thr Leu Arg Gly Met Gly
                 80                  85                  90

CAG AAC TCT GTC GAC ATC AAG GTG GAC AAC GCC TAT TCC GAC AGC CAA        638
Gln Asn Ser Val Asp Ile Lys Val Asp Asn Ala Tyr Ser Asp Ser Gln
             95                 100                 105

ATC CTT TAC CAC CAA GGC AGA TTT ATT GTC GAT CCC GCT TTG GTT AAA        686
Ile Leu Tyr His Gln Gly Arg Phe Ile Val Asp Pro Ala Leu Val Lys
        110                 115                 120

GTC GTT TCC GTA CAG AAA GGC GCG GGT TCC GCC TCT GCC GGT ATC GGC        734
Val Val Ser Val Gln Lys Gly Ala Gly Ser Ala Ser Ala Gly Ile Gly
    125                 130                 135

GCG ACC AAC GGC GCG ATC ATC GCC AAA ACC GTC GAT GCC CAA GAC CTG        782
Ala Thr Asn Gly Ala Ile Ile Ala Lys Thr Val Asp Ala Gln Asp Leu
140                 145                 150                 155

CTC AAA GGC TTG GAT AAA AAC TGG GGC GTG CGC CTC AAC AGC GGC TTT        830
Leu Lys Gly Leu Asp Lys Asn Trp Gly Val Arg Leu Asn Ser Gly Phe
                160                 165                 170

GCC GGC AAC AAC GGC GCA AGC TAC GGC GCA AGC GTA TTC GGA AAA GAG        878
Ala Gly Asn Asn Gly Ala Ser Tyr Gly Ala Ser Val Phe Gly Lys Glu
            175                 180                 185

GGC AAC TTC GAC GGT TTG TTC TCT TAC AAC CGC AAC GAT GAA AAA GAT        926
Gly Asn Phe Asp Gly Leu Phe Ser Tyr Asn Arg Asn Asp Glu Lys Asp
        190                 195                 200

TAC GAA GCC GGC AAA GGT TTC CGC AAT GAC AAC GGC GGC AAA ACC GTA        974
Tyr Glu Ala Gly Lys Gly Phe Arg Asn Asp Asn Gly Gly Lys Thr Val
205                 210                 215

CCG TAC AGC GCG CTG GAC AAA CGC AGC TAC CTC GCC AAA ATC GGA ACA       1022
Pro Tyr Ser Ala Leu Asp Lys Arg Ser Tyr Leu Ala Lys Ile Gly Thr
220                 225                 230                 235

ACC TTC GGC GAC GGC GAC CAC CGC ATC GTG TTG AGC CAT ATG AAA GAC       1070
Thr Phe Gly Asp Gly Asp His Arg Ile Val Leu Ser His Met Lys Asp
                240                 245                 250

CAA CAC CGG GGC ATC CGC ACT GTG CGT GAA GAG TTT GCC GTC AGC GAA       1118
Gln His Arg Gly Ile Arg Thr Val Arg Glu Glu Phe Ala Val Ser Glu
            255                 260                 265

AAA AAT TCA CGG ATA ACT ATT AAA CGC CAA GCC CCA TCC TAC CGC GAA       1166
Lys Asn Ser Arg Ile Thr Ile Lys Arg Gln Ala Pro Ser Tyr Arg Glu
        270                 275                 280

ACC ACT CAA TCC AAC ACC AAC TTG GCG TAC ACC GGC AAA GAT TTG GGC       1214
Thr Thr Gln Ser Asn Thr Asn Leu Ala Tyr Thr Gly Lys Asp Leu Gly
285                 290                 295

TTT GTC GAA AAA CTG GAT GCC AAC GCC TAT GTG TTG GAA AAG AAA CGC       1262
Phe Val Glu Lys Leu Asp Ala Asn Ala Tyr Val Leu Glu Lys Lys Arg
300                 305                 310                 315

TAT TCC GCC GAT GAC AAA GAT AAC GGC TAC GCA GGC AAT GTA AAA GGC       1310
Tyr Ser Ala Asp Asp Lys Asp Asn Gly Tyr Ala Gly Asn Val Lys Gly
                320                 325                 330

CCC AAC CAT ACC CGA ATC GCC ACT CGG AGT ATG AAC TTC AAC TTC GAC       1358
Pro Asn His Thr Arg Ile Ala Thr Arg Ser Met Asn Phe Asn Phe Asp
            335                 340                 345

AGC CGC CTT GCC GAA CAA ACC CTG TTG AAA TAC GGC ATC AAC TAC CGC       1406
Ser Arg Leu Ala Glu Gln Thr Leu Leu Lys Tyr Gly Ile Asn Tyr Arg
        350                 355                 360

CAT CAG GAA ATC AAA CCG CAA GCG TTT TTG AAC TCG GAA TTT GAA ATA       1454
```

```
                                                              -continued

His Gln Glu Ile Lys Pro Gln Ala Phe Leu Asn Ser Glu Phe Glu Ile
    365             370                 375

AAA GAT AAA GAA AAA GCA ACT AAT GAA GAG AAA AAG AAG AAC CGT GAA     1502
Lys Asp Lys Glu Lys Ala Thr Asn Glu Glu Lys Lys Lys Asn Arg Glu
380             385                 390                 395

AAT GAA AAA ATT GCC AAA GCC TAC CGC CTG ACC AAC CCG ACC AAA ACC     1550
Asn Glu Lys Ile Ala Lys Ala Tyr Arg Leu Thr Asn Pro Thr Lys Thr
                400                 405                 410

GAT ACC GGC GCG TAT ATC GAA GCC ATT CAC GAG ATT GAC GGC TTT ACC     1598
Asp Thr Gly Ala Tyr Ile Glu Ala Ile His Glu Ile Asp Gly Phe Thr
                415                 420                 425

CTG ACC GGC GGG CTG CGT TAC GAC CGC TTC AAG GTG AAA ACC CAC GAC     1646
Leu Thr Gly Gly Leu Arg Tyr Asp Arg Phe Lys Val Lys Thr His Asp
            430                 435                 440

GGC AAA ACC GTT TCA AGC AGC AGC CTC AAC CCG AGT TTC GGC GTG ATT     1694
Gly Lys Thr Val Ser Ser Ser Ser Leu Asn Pro Ser Phe Gly Val Ile
            445                 450                 455

TGG CAG CCG CGC GAA CAC TGG AGC TTC AGC GCG AGC CAC AAC TAC GCC     1742
Trp Gln Pro Arg Glu His Trp Ser Phe Ser Ala Ser His Asn Tyr Ala
460             465                 470                 475

GGC CGC AGC CCG CGC CTG TAT GAC GCT CTG CAA ACC CAC GGC AAG CGC     1790
Gly Arg Ser Pro Arg Leu Tyr Asp Ala Leu Gln Thr His Gly Lys Arg
                480                 485                 490

GGC ATC ATC TCG ATT GCC GAC GGC ACG AAA GCC GAA CGC GCG CGC AAT     1838
Gly Ile Ile Ser Ile Ala Asp Gly Thr Lys Ala Glu Arg Ala Arg Asn
                495                 500                 505

ACC GAA ATC GGC TTC AAC TAC AAC GAC GGC ACG TTT GCC GCA AAC GGC     1886
Thr Glu Ile Gly Phe Asn Tyr Asn Asp Gly Thr Phe Ala Ala Asn Gly
            510                 515                 520

AGC TAC TTC CGG CAG ACC ATC AAA GAC GCG CTT GCC AAT CCG CAA AAC     1934
Ser Tyr Phe Arg Gln Thr Ile Lys Asp Ala Leu Ala Asn Pro Gln Asn
525             530                 535

CGC CAC GAC TCC GTC GCC GTC CGC GAA GCC GTC AAC GCC GGC TAC ATC     1982
Arg His Asp Ser Val Ala Val Arg Glu Ala Val Asn Ala Gly Tyr Ile
540             545                 550                 555

AAA AAC CAC GGT TAC GAA TTG GGC GCG TCC TAC CGC ACC GGC GGC CTG     2030
Lys Asn His Gly Tyr Glu Leu Gly Ala Ser Tyr Arg Thr Gly Gly Leu
                560                 565                 570

ACC GCC AAA GTC GGC GTA AGC CAC AGC AAA CCG CGC TTT TAC GAT ACG     2078
Thr Ala Lys Val Gly Val Ser His Ser Lys Pro Arg Phe Tyr Asp Thr
                575                 580                 585

CAC AAA GAC AAG CTG TTG AGC GCG AAC CCT GAA TTT GGC GCA CAA GTC     2126
His Lys Asp Lys Leu Leu Ser Ala Asn Pro Glu Phe Gly Ala Gln Val
            590                 595                 600

GGC CGC ACT TGG ACG GCC TCC CTT GCC TAC CGC TTC AAA AAC CCG AAT     2174
Gly Arg Thr Trp Thr Ala Ser Leu Ala Tyr Arg Phe Lys Asn Pro Asn
605             610                 615

CTG GAA ATC GGC TGG CGC GGT CGT TAT GTT CAA AAA GCC GTG GGT TCG     2222
Leu Glu Ile Gly Trp Arg Gly Arg Tyr Val Gln Lys Ala Val Gly Ser
620             625                 630                 635

ATA TTG GCG GCA GGT CAA AAA GAC CGC GAC GGC AAA TTG GAA AAC GTT     2270
Ile Leu Ala Ala Gly Gln Lys Asp Arg Asp Gly Lys Leu Glu Asn Val
                640                 645                 650

GTA CGC CAA GGT TTC GGT GTG AAC GAT GTC TTC GCC AAC TGG AAA CCG     2318
Val Arg Gln Gly Phe Gly Val Asn Asp Val Phe Ala Asn Trp Lys Pro
            655                 660                 665

CTG GGC AAA GAC ACG CTC AAT GTT AAT CTT TCG GTT AAC AAC GTG TTC     2366
Leu Gly Lys Asp Thr Leu Asn Val Asn Leu Ser Val Asn Asn Val Phe
            670                 675                 680
```

```
GAC AAG TTC TAC TAT CCG CAC AGC CAA CGC TGG ACC AAT ACC CTG CCG    2414
Asp Lys Phe Tyr Tyr Pro His Ser Gln Arg Trp Thr Asn Thr Leu Pro
        685                 690                 695

GGC GTG GGA CGT GAT GTA CGC CTG GGC GTG AAC TAC AAG TTC            2456
Gly Val Gly Arg Asp Val Arg Leu Gly Val Asn Tyr Lys Phe
700                 705                 710

TAAAACGCAC ATCCCGAAAA AATGCCGTCT GAAAGCCTTT CAGACGGCAT CTGTCCTGAT   2516

AATTTGATAT ATAGTGGATT AACAAAAACC GGTACGGCGT TGCCCCGCCT TAGCTCAAAG   2576

GGAACGATTC CCTAAGGTGC TGAA                                          2600
```

(2) INFORMATION FOR SEQ ID NO:2:

(i) SEQUENCE CHARACTERISTICS:
        (A) LENGTH: 713 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asn Ala Pro Phe Phe Arg Leu Ser Leu Leu Ser Leu Thr Leu Ala
1               5                   10                  15

Ala Gly Phe Ala His Ala Ala Glu Asn Asn Ala Asn Val Ala Leu Asp
            20                  25                  30

Thr Val Thr Val Lys Gly Asp Arg Gln Gly Ser Lys Ile Arg Thr Asn
        35                  40                  45

Ile Val Thr Leu Gln Gln Lys Asp Glu Ser Thr Ala Thr Asp Met Arg
    50                  55                  60

Glu Leu Leu Lys Glu Glu Pro Ser Ile Asp Phe Gly Gly Gly Asn Gly
65                  70                  75                  80

Thr Ser Gln Phe Leu Thr Leu Arg Gly Met Gly Gln Asn Ser Val Asp
                85                  90                  95

Ile Lys Val Asp Asn Ala Tyr Ser Asp Ser Gln Ile Leu Tyr His Gln
            100                 105                 110

Gly Arg Phe Ile Val Asp Pro Ala Leu Val Lys Val Val Ser Val Gln
        115                 120                 125

Lys Gly Ala Gly Ser Ala Ser Ala Gly Ile Gly Ala Thr Asn Gly Ala
    130                 135                 140

Ile Ile Ala Lys Thr Val Asp Ala Gln Asp Leu Leu Lys Gly Leu Asp
145                 150                 155                 160

Lys Asn Trp Gly Val Arg Leu Asn Ser Gly Phe Ala Gly Asn Asn Gly
                165                 170                 175

Ala Ser Tyr Gly Ala Ser Val Phe Gly Lys Glu Gly Asn Phe Asp Gly
            180                 185                 190

Leu Phe Ser Tyr Asn Arg Asn Asp Glu Lys Asp Tyr Glu Ala Gly Lys
        195                 200                 205

Gly Phe Arg Asn Asp Asn Gly Gly Lys Thr Val Pro Tyr Ser Ala Leu
    210                 215                 220

Asp Lys Arg Ser Tyr Leu Ala Lys Ile Gly Thr Thr Phe Gly Asp Gly
225                 230                 235                 240

Asp His Arg Ile Val Leu Ser His Met Lys Asp Gln His Arg Gly Ile
                245                 250                 255

Arg Thr Val Arg Glu Glu Phe Ala Val Ser Glu Lys Asn Ser Arg Ile
            260                 265                 270

Thr Ile Lys Arg Gln Ala Pro Ser Tyr Arg Glu Thr Thr Gln Ser Asn
        275                 280                 285
```

```
Thr Asn Leu Ala Tyr Thr Gly Lys Asp Leu Gly Phe Val Glu Lys Leu
    290                 295                 300

Asp Ala Asn Ala Tyr Val Leu Glu Lys Lys Arg Tyr Ser Ala Asp Asp
305                 310                 315                 320

Lys Asp Asn Gly Tyr Ala Gly Asn Val Lys Gly Pro Asn His Thr Arg
                325                 330                 335

Ile Ala Thr Arg Ser Met Asn Phe Asn Phe Asp Ser Arg Leu Ala Glu
                340                 345                 350

Gln Thr Leu Leu Lys Tyr Gly Ile Asn Tyr Arg His Gln Glu Ile Lys
                355                 360                 365

Pro Gln Ala Phe Leu Asn Ser Glu Phe Glu Ile Lys Asp Lys Glu Lys
    370                 375                 380

Ala Thr Asn Glu Glu Lys Lys Asn Arg Glu Asn Glu Lys Ile Ala
385                 390                 395                 400

Lys Ala Tyr Arg Leu Thr Asn Pro Thr Lys Thr Asp Thr Gly Ala Tyr
                405                 410                 415

Ile Glu Ala Ile His Glu Ile Asp Gly Phe Thr Leu Thr Gly Gly Leu
                420                 425                 430

Arg Tyr Asp Arg Phe Lys Val Lys Thr His Asp Gly Lys Thr Val Ser
            435                 440                 445

Ser Ser Ser Leu Asn Pro Ser Phe Gly Val Ile Trp Gln Pro Arg Glu
    450                 455                 460

His Trp Ser Phe Ser Ala Ser His Asn Tyr Ala Gly Arg Ser Pro Arg
465                 470                 475                 480

Leu Tyr Asp Ala Leu Gln Thr His Gly Lys Arg Gly Ile Ile Ser Ile
                485                 490                 495

Ala Asp Gly Thr Lys Ala Glu Arg Ala Arg Asn Thr Glu Ile Gly Phe
            500                 505                 510

Asn Tyr Asn Asp Gly Thr Phe Ala Ala Asn Gly Ser Tyr Phe Arg Gln
    515                 520                 525

Thr Ile Lys Asp Ala Leu Ala Asn Pro Gln Asn Arg His Asp Ser Val
    530                 535                 540

Ala Val Arg Glu Ala Val Asn Ala Gly Tyr Ile Lys Asn His Gly Tyr
545                 550                 555                 560

Glu Leu Gly Ala Ser Tyr Arg Thr Gly Leu Thr Ala Lys Val Gly
                565                 570                 575

Val Ser His Ser Lys Pro Arg Phe Tyr Asp Thr His Lys Asp Lys Leu
            580                 585                 590

Leu Ser Ala Asn Pro Glu Phe Gly Ala Gln Val Gly Arg Thr Trp Thr
        595                 600                 605

Ala Ser Leu Ala Tyr Arg Phe Lys Asn Pro Asn Leu Glu Ile Gly Trp
    610                 615                 620

Arg Gly Arg Tyr Val Gln Lys Ala Val Gly Ser Ile Leu Ala Ala Gly
625                 630                 635                 640

Gln Lys Asp Arg Asp Gly Lys Leu Glu Asn Val Val Arg Gln Gly Phe
                645                 650                 655

Gly Val Asn Asp Val Phe Ala Asn Trp Lys Pro Leu Gly Lys Asp Thr
                660                 665                 670

Leu Asn Val Asn Leu Ser Val Asn Asn Val Phe Asp Lys Phe Tyr Tyr
            675                 680                 685

Pro His Ser Gln Arg Trp Thr Asn Thr Leu Pro Gly Val Gly Arg Asp
    690                 695                 700
```

```
Val Arg Leu Gly Val Asn Tyr Lys Phe
705                 710
```

(2) INFORMATION FOR SEQ ID NO:3:

(i) SEQUENCE CHARACTERISTICS:
        (A) LENGTH: 2381 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 172..2313

(xi) SEQUENCE DESCRIPTION: SEQ ID NO:3:

```
ATAAGTACAC TCAACAAAAA ACAACGCTTC GCAAATAAAA ACGATAATCA GCTTTACACA      60

ACCCCCCCCC CCGCTAATAT AAACAAAAAT AATTATTATT ATTTTTTCTT ATCCTGCCAA     120

ACCTTAACGG TTTGGCTTAA CTTCCCTTCA TACACTCAAA AGGACGAACA A ATG AAC     177
                                                         Met Asn
                                                           1

GCC CCG TTT TTC CGC CTC AGC CTG CTC TCG CTC ACA CTT GCC GCC GGC     225
Ala Pro Phe Phe Arg Leu Ser Leu Leu Ser Leu Thr Leu Ala Ala Gly
         5                  10                  15

TTT GCC CAC GCG GCA GAA AAT AAT GCC AAT GTC GCA TTG GAT ACC GTT     273
Phe Ala His Ala Ala Glu Asn Asn Ala Asn Val Ala Leu Asp Thr Val
     20                  25                  30

ACC GTA AAA GGC GAC CGC CAA GGC AGC AAA ATC CGT ACC AAC ATC GTT     321
Thr Val Lys Gly Asp Arg Gln Gly Ser Lys Ile Arg Thr Asn Ile Val
 35                  40                  45                  50

ACG CTT CAA CAA AAA GAC GAA AGC ACC GCA ACC GAT ATG CGC GAA CTC     369
Thr Leu Gln Gln Lys Asp Glu Ser Thr Ala Thr Asp Met Arg Glu Leu
                 55                  60                  65

TTA AAA GAA GAG CCC TCC ATC GAT TTC GGC GGC GGC AAC GGC ACG TCC     417
Leu Lys Glu Glu Pro Ser Ile Asp Phe Gly Gly Gly Asn Gly Thr Ser
             70                  75                  80

CAA TTC CTG ACG CTG CGC GGC ATG GGT CAG AAC TCT GTC GAC ATC AAG     465
Gln Phe Leu Thr Leu Arg Gly Met Gly Gln Asn Ser Val Asp Ile Lys
         85                  90                  95

GTG GAC AAC GCC TAT TCC GAC AGC CAA ATC CTT TAC CAC CAA GGC AGA     513
Val Asp Asn Ala Tyr Ser Asp Ser Gln Ile Leu Tyr His Gln Gly Arg
    100                 105                 110

TTT ATT GTC GAT CCC GCT TTG GTT AAA GTC GTT TCC GTA CAA AAA GGC     561
Phe Ile Val Asp Pro Ala Leu Val Lys Val Val Ser Val Gln Lys Gly
115                 120                 125                 130

GCG GGT TCC GCC TCT GCC GGT ATC GGC GCG ACC AAC GGC GCG ATT ATC     609
Ala Gly Ser Ala Ser Ala Gly Ile Gly Ala Thr Asn Gly Ala Ile Ile
                135                 140                 145

GCC AAA ACC GTC GAT GCC CAA GAC CTG CTC AAA GGC TTG GAT AAA AAC     657
Ala Lys Thr Val Asp Ala Gln Asp Leu Leu Lys Gly Leu Asp Lys Asn
            150                 155                 160

TGG GGC GTG CGC CTC AAC AGC GGC TTT GCC GGC AAC AAC GGC GTA AGC     705
Trp Gly Val Arg Leu Asn Ser Gly Phe Ala Gly Asn Asn Gly Val Ser
        165                 170                 175

TAC GGC GCA AGC GTA TTC GGA AAA GAG GGC AAC TTC GAC GGT TTG TTC     753
Tyr Gly Ala Ser Val Phe Gly Lys Glu Gly Asn Phe Asp Gly Leu Phe
    180                 185                 190

TCT TAC AAC CGC AAC GAT GAA AAA GAT TAC GAA GCC GGC AAA GGC TTC     801
Ser Tyr Asn Arg Asn Asp Glu Lys Asp Tyr Glu Ala Gly Lys Gly Phe
195                 200                 205                 210
```

```
CGC AAT GTC AAC GGC GGC AAA ACC GTA CCG TAC AGC GCG CTG GAC AAA         849
Arg Asn Val Asn Gly Gly Lys Thr Val Pro Tyr Ser Ala Leu Asp Lys
                215                 220                 225

CGC AGC TAC CTC GCC AAA ATC GGA ACA ACC TTC GGC GAC GGC GAC CAC         897
Arg Ser Tyr Leu Ala Lys Ile Gly Thr Thr Phe Gly Asp Gly Asp His
                230                 235                 240

CGC ATC GTA TTG AGC CAT ATG AAA GAC CAA CAC CGG GGC ATC CGC ACT         945
Arg Ile Val Leu Ser His Met Lys Asp Gln His Arg Gly Ile Arg Thr
                245                 250                 255

GTG CGT GAA GAG TTT GCC GTC GGC GGC GAA AAT TCA CGG ATA ACT ATT         993
Val Arg Glu Glu Phe Ala Val Gly Gly Glu Asn Ser Arg Ile Thr Ile
260                 265                 270

AAA CGC CAA GCC CCT GCC TAC CGC GAA ACC ACA CAA TCC AAC ACC AAT        1041
Lys Arg Gln Ala Pro Ala Tyr Arg Glu Thr Thr Gln Ser Asn Thr Asn
275                 280                 285                 290

TTG GCG TAC ACC GGC AAA GAT TTG GGC TTT GTC GAA AAA CTG GAT GCC        1089
Leu Ala Tyr Thr Gly Lys Asp Leu Gly Phe Val Glu Lys Leu Asp Ala
                295                 300                 305

AAC GCC TAT GTG CTG GAA AAA AAA CGC TAT TCC GCC GAT GAC AAA GAT        1137
Asn Ala Tyr Val Leu Glu Lys Lys Arg Tyr Ser Ala Asp Asp Lys Asp
                310                 315                 320

AAC GGC TAC GCA GGC AAT GTA AAA GGC CCC AAC CAT ACC CGA ATC GCC        1185
Asn Gly Tyr Ala Gly Asn Val Lys Gly Pro Asn His Thr Arg Ile Ala
                325                 330                 335

ACT CGG GGC ATG AAC TTC AAC TTC GAC AGC CGC CTT GCC GAA CAA ACC        1233
Thr Arg Gly Met Asn Phe Asn Phe Asp Ser Arg Leu Ala Glu Gln Thr
                340                 345                 350

CTG TTG AAA TAC GGC ATC AAC TAC CGC CAT CAG GAA ATC AAA CCG CAA        1281
Leu Leu Lys Tyr Gly Ile Asn Tyr Arg His Gln Glu Ile Lys Pro Gln
355                 360                 365                 370

GCG TTT TTG AAT TCA CAA TTT AAA ATT GAA GAT AAA AAA GAT GCA ACT        1329
Ala Phe Leu Asn Ser Gln Phe Lys Ile Glu Asp Lys Lys Asp Ala Thr
                375                 380                 385

GAG GAA GAT AAA AAG AAG AAC CGT GAA AAT GAA AAA ATT GCC AAA GCC        1377
Glu Glu Asp Lys Lys Lys Asn Arg Glu Asn Glu Lys Ile Ala Lys Ala
                390                 395                 400

TAC CGT CTG ACC AAC CCG ACC AAA ACC GAT ACC GGC GCG TAT ATC GAA        1425
Tyr Arg Leu Thr Asn Pro Thr Lys Thr Asp Thr Gly Ala Tyr Ile Glu
                405                 410                 415

GCC ATT CAC GAG ATT GAC GGC TTT ACC CTG ACC GGC GGG CTG CGT TAC        1473
Ala Ile His Glu Ile Asp Gly Phe Thr Leu Thr Gly Gly Leu Arg Tyr
420                 425                 430

GAC CGC TTC AAG GTG AAA ACC CAC GAC GGC AAA ACC GTT TCA AGC AGC        1521
Asp Arg Phe Lys Val Lys Thr His Asp Gly Lys Thr Val Ser Ser Ser
435                 440                 445                 450

AGC CTC AAC CCG AGT TTC GGC GTG ATT TGG CAG CCG CGC GAA CAC TGG        1569
Ser Leu Asn Pro Ser Phe Gly Val Ile Trp Gln Pro Arg Glu His Trp
                455                 460                 465

AGC TTC AGC GCG AGC CAC AAC TAC GCC AGC CGC AGC CCG CGC CTG TAT        1617
Ser Phe Ser Ala Ser His Asn Tyr Ala Ser Arg Ser Pro Arg Leu Tyr
                470                 475                 480

GAC GCG CTG CAA ACC CAC GGC AAA CGC GGC ATC ATC TCG ATT GCC GAC        1665
Asp Ala Leu Gln Thr His Gly Lys Arg Gly Ile Ile Ser Ile Ala Asp
                485                 490                 495

GGC ACC AAA GCC GAA CGC GCG CGC AAT ACC GAA ATC GGC TTC AAC TAC        1713
Gly Thr Lys Ala Glu Arg Ala Arg Asn Thr Glu Ile Gly Phe Asn Tyr
                500                 505                 510

AAC GAC GGC ACG TTT GCC GCA AAC GGC AGC TAC TTC CGG CAG ACC ATC        1761
Asn Asp Gly Thr Phe Ala Ala Asn Gly Ser Tyr Phe Arg Gln Thr Ile
```

-continued

```
           515                 520                 525                 530
AAA GAC GCG CTT GCC AAT CCG CAA AAC CGC CAC GAC TCT GTC GCC GTC            1809
Lys Asp Ala Leu Ala Asn Pro Gln Asn Arg His Asp Ser Val Ala Val
                535                 540                 545

CGC GAA GCC GTC AAC GCC GGC TAC ATC AAA AAC CAC GGT TAC GAA TTG            1857
Arg Glu Ala Val Asn Ala Gly Tyr Ile Lys Asn His Gly Tyr Glu Leu
                550                 555                 560

GGC GCG TCC TAC CGC ACC GGC GGC CTG ACC GCC AAA GTC GGC GTA AGC            1905
Gly Ala Ser Tyr Arg Thr Gly Gly Leu Thr Ala Lys Val Gly Val Ser
                565                 570                 575

CGC AGC AAA CCG CGC TTT TAC GAT ACC CAT CCT AAA AAA CTG TTG AGC            1953
Arg Ser Lys Pro Arg Phe Tyr Asp Thr His Pro Lys Lys Leu Leu Ser
                580                 585                 590

GCG AAC CCC GAG TTT GGC GCA CAA ACC GGC CGC ACT TGG ACG GCC TCC            2001
Ala Asn Pro Glu Phe Gly Ala Gln Thr Gly Arg Thr Trp Thr Ala Ser
595                 600                 605                 610

CTT GCC TAC CGC TTC AAA AAC CCG AAT CTG GAA ATC GGC TGG CGC GGA            2049
Leu Ala Tyr Arg Phe Lys Asn Pro Asn Leu Glu Ile Gly Trp Arg Gly
                615                 620                 625

CGC TAT GTT CAA AAA GCT ACG GGT TCG ATA TTG GCG GCA GGG CAA AAA            2097
Arg Tyr Val Gln Lys Ala Thr Gly Ser Ile Leu Ala Ala Gly Gln Lys
                630                 635                 640

GAC CGC GAC GGC AAA TTG GAA AAC GTT GTA CGC CAA GGT TTC GGT GTG            2145
Asp Arg Asp Gly Lys Leu Glu Asn Val Val Arg Gln Gly Phe Gly Val
                645                 650                 655

AAC GAT GTC TTC GCC AAC TGG AAA CCG CTG GGC AAA GAC ACG CTC AAT            2193
Asn Asp Val Phe Ala Asn Trp Lys Pro Leu Gly Lys Asp Thr Leu Asn
660                 665                 670

GTT AAT CTT TCG GTT AAC AAC GTG TTC GAC AAG TTC TAC TAT CCG CAC            2241
Val Asn Leu Ser Val Asn Asn Val Phe Asp Lys Phe Tyr Tyr Pro His
675                 680                 685                 690

AGC CAA CGC TGG ACC AAT ACC CTG CCG GGC GTG GGA CGT GAT GTA CGC            2289
Ser Gln Arg Trp Thr Asn Thr Leu Pro Gly Val Gly Arg Asp Val Arg
                695                 700                 705

CTG GGC GTG AAC TAC AAG TTC TAAAACGCAC ATCCCGAAAA AATGCCGTCT               2340
Leu Gly Val Asn Tyr Lys Phe
                710

GAAAGCCTTT CAGACGGCAT CTGTCCTGAT AATTTGATAT A                              2381
```

(2) INFORMATION FOR SEQ ID NO:4:

(i) SEQUENCE CHARACTERISTICS:
        (A) LENGTH: 713 amino acids
        (B) TYPE: amino acid
        (D) TOPOLOGY: linear (ii) MOLECULE TYPE: protein (xi) SEQUENCE DESCRIPTION: SEQ ID NO:4:

```
Met Asn Ala Pro Phe Phe Arg Leu Ser Leu Leu Ser Leu Thr Leu Ala
1               5                   10                  15

Ala Gly Phe Ala His Ala Ala Glu Asn Asn Ala Asn Val Ala Leu Asp
                20                  25                  30

Thr Val Thr Val Lys Gly Asp Arg Gln Gly Ser Lys Ile Arg Thr Asn
                35                  40                  45

Ile Val Thr Leu Gln Gln Lys Asp Glu Ser Thr Ala Thr Asp Met Arg
        50                  55                  60

Glu Leu Leu Lys Glu Glu Pro Ser Ile Asp Phe Gly Gly Gly Asn Gly
65              70                  75                  80
```

-continued

```
Thr Ser Gln Phe Leu Thr Leu Arg Gly Met Gly Gln Asn Ser Val Asp
                 85                  90                  95
Ile Lys Val Asp Asn Ala Tyr Ser Asp Ser Gln Ile Leu Tyr His Gln
            100                 105                 110
Gly Arg Phe Ile Val Asp Pro Ala Leu Val Lys Val Ser Val Gln
        115                 120                 125
Lys Gly Ala Gly Ser Ala Ser Ala Gly Ile Gly Ala Thr Asn Gly Ala
130                 135                 140
Ile Ile Ala Lys Thr Val Asp Ala Gln Asp Leu Leu Lys Gly Leu Asp
145                 150                 155                 160
Lys Asn Trp Gly Val Arg Leu Asn Ser Gly Phe Ala Gly Asn Asn Gly
                165                 170                 175
Val Ser Tyr Gly Ala Ser Val Phe Gly Lys Glu Gly Asn Phe Asp Gly
            180                 185                 190
Leu Phe Ser Tyr Asn Arg Asn Asp Glu Lys Asp Tyr Glu Ala Gly Lys
        195                 200                 205
Gly Phe Arg Asn Val Asn Gly Gly Lys Thr Val Pro Tyr Ser Ala Leu
    210                 215                 220
Asp Lys Arg Ser Tyr Leu Ala Lys Ile Gly Thr Thr Phe Gly Asp Gly
225                 230                 235                 240
Asp His Arg Ile Val Leu Ser His Met Lys Asp Gln His Arg Gly Ile
                245                 250                 255
Arg Thr Val Arg Glu Glu Phe Ala Val Gly Gly Glu Asn Ser Arg Ile
            260                 265                 270
Thr Ile Lys Arg Gln Ala Pro Ala Tyr Arg Glu Thr Thr Gln Ser Asn
        275                 280                 285
Thr Asn Leu Ala Tyr Thr Gly Lys Asp Leu Gly Phe Val Glu Lys Leu
    290                 295                 300
Asp Ala Asn Ala Tyr Val Leu Glu Lys Lys Arg Tyr Ser Ala Asp Asp
305                 310                 315                 320
Lys Asp Asn Gly Tyr Ala Gly Asn Val Lys Gly Pro Asn His Thr Arg
                325                 330                 335
Ile Ala Thr Arg Gly Met Asn Phe Asn Phe Asp Ser Arg Leu Ala Glu
            340                 345                 350
Gln Thr Leu Leu Lys Tyr Gly Ile Asn Tyr Arg His Gln Glu Ile Lys
        355                 360                 365
Pro Gln Ala Phe Leu Asn Ser Gln Phe Lys Ile Glu Asp Lys Lys Asp
    370                 375                 380
Ala Thr Glu Glu Asp Lys Lys Asn Arg Glu Asn Glu Lys Ile Ala
385                 390                 395                 400
Lys Ala Tyr Arg Leu Thr Asn Pro Thr Lys Thr Asp Thr Gly Ala Tyr
                405                 410                 415
Ile Glu Ala Ile His Glu Ile Asp Gly Phe Thr Leu Thr Gly Gly Leu
            420                 425                 430
Arg Tyr Asp Arg Phe Lys Val Lys Thr His Asp Gly Lys Thr Val Ser
        435                 440                 445
Ser Ser Ser Leu Asn Pro Ser Phe Gly Val Ile Trp Gln Pro Arg Glu
    450                 455                 460
His Trp Ser Phe Ser Ala Ser His Asn Tyr Ala Ser Arg Ser Pro Arg
465                 470                 475                 480
Leu Tyr Asp Ala Leu Gln Thr His Gly Lys Arg Gly Ile Ile Ser Ile
                485                 490                 495
Ala Asp Gly Thr Lys Ala Glu Arg Ala Arg Asn Thr Glu Ile Gly Phe
```

―continued

```
                    500                     505                     510
Asn Tyr Asn Asp Gly Thr Phe Ala Ala Asn Gly Ser Tyr Phe Arg Gln
            515                     520                     525

Thr Ile Lys Asp Ala Leu Ala Asn Pro Gln Asn Arg His Asp Ser Val
    530                     535                     540

Ala Val Arg Glu Ala Val Asn Ala Gly Tyr Ile Lys Asn His Gly Tyr
545                     550                     555                     560

Glu Leu Gly Ala Ser Tyr Arg Thr Gly Gly Leu Thr Ala Lys Val Gly
                565                     570                     575

Val Ser Arg Ser Lys Pro Arg Phe Tyr Asp Thr His Pro Lys Lys Leu
                580                     585                     590

Leu Ser Ala Asn Pro Glu Phe Gly Ala Gln Thr Gly Arg Thr Trp Thr
            595                     600                     605

Ala Ser Leu Ala Tyr Arg Phe Lys Asn Pro Asn Leu Glu Ile Gly Trp
            610                     615                     620

Arg Gly Arg Tyr Val Gln Lys Ala Thr Gly Ser Ile Leu Ala Ala Gly
625                     630                     635                     640

Gln Lys Asp Arg Asp Gly Lys Leu Glu Asn Val Val Arg Gln Gly Phe
                645                     650                     655

Gly Val Asn Asp Val Phe Ala Asn Trp Lys Pro Leu Gly Lys Asp Thr
                660                     665                     670

Leu Asn Val Asn Leu Ser Val Asn Asn Val Phe Asp Lys Phe Tyr Tyr
            675                     680                     685

Pro His Ser Gln Arg Trp Thr Asn Thr Leu Pro Gly Val Gly Arg Asp
            690                     695                     700

Val Arg Leu Gly Val Asn Tyr Lys Phe
705                     710
```